United States Patent
Eghbal et al.

(10) Patent No.: US 11,390,901 B2
(45) Date of Patent: Jul. 19, 2022

(54) APPARATUS AND METHOD FOR ANALYZING BIOLOGICAL INDICATORS

(71) Applicant: ASP Global Manufacturing GmbH, Schaffhausen (CH)

(72) Inventors: Darius D. Eghbal, Sierra Madre, CA (US); Jacob S. Childs, Huntington Beach, CA (US); Margaret D. Shaffer, San Clemente, CA (US); Jeremy M. Yarwood, Aliso Viejo, CA (US); Benjamin M. Fryer, Lake Forest, CA (US); Howell B. Schwartz, Irvine, CA (US)

(73) Assignee: ASP Global Manufacturing GmbH, Schaffhausen (CH)

( * ) Notice: Subject to any disclaimer, the term of this patent is extended or adjusted under 35 U.S.C. 154(b) by 370 days.

(21) Appl. No.: 16/567,587

(22) Filed: Sep. 11, 2019

(65) Prior Publication Data
US 2020/0063179 A1 Feb. 27, 2020

Related U.S. Application Data

(62) Division of application No. 15/441,734, filed on Feb. 24, 2017, now Pat. No. 10,443,086.
(Continued)

(51) Int. Cl.
*C12Q 1/22* (2006.01)
*A61L 2/28* (2006.01)
(Continued)

(52) U.S. Cl.
CPC .................. *C12Q 1/22* (2013.01); *A61L 2/28* (2013.01); *G01N 21/6428* (2013.01);
(Continued)

(58) Field of Classification Search
CPC ......... C12Q 1/22; A61L 2/28; G01N 21/6428; G01N 21/6452; G01N 21/94; G01N 33/48792; G01N 2021/6439
See application file for complete search history.

(56) References Cited

U.S. PATENT DOCUMENTS 5,863,790 A  1/1999  Bolea
5,955,296 A  9/1999  Roll
(Continued)

FOREIGN PATENT DOCUMENTS

CN  1492769 A  4/2004
CN  1663618 A  9/2005
(Continued)

OTHER PUBLICATIONS https://web.archive.org/web/20150930181305/https://content.pattersondental.com/items/PDFs/images/214105.pdf published on Sep. 30, 2015, 1 page, and hereinafter "color change guide" (Year: 2015).*
(Continued)

*Primary Examiner* — Benjamin R Whatley
(74) *Attorney, Agent, or Firm* — Frost Brown Todd LLC

(57) ABSTRACT

A biological indicator analyzer includes a plurality of wells, a plurality of organism detector features, and a user input feature such as a touch screen. Each well is configured to receive a respective biological indicator. Each organism detector feature is configured to detect whether a biological indicator disposed in a corresponding well of the plurality of wells contains a living organism. The touch screen is configured to receive user input and provide information to the user indicating a status of biological indicator analysis. The biological indicator analyzer may be used to analyze a biological indicator that was positioned in a sterilization chamber of a sterilizing cabinet along with at least one medical device that is to be sterilized. The analysis may
(Continued)

indicate whether the sterilization cycle in the sterilization chamber as successful.

21 Claims, 16 Drawing Sheets

Related U.S. Application Data

(60) Provisional application No. 62/376,517, filed on Aug. 18, 2016, provisional application No. 62/316,722, filed on Apr. 1, 2016, provisional application No. 62/302,257, filed on Mar. 2, 2016.

(51) Int. Cl.
   *G01N 21/64* (2006.01)
   *G01N 21/94* (2006.01)
   *G01N 33/487* (2006.01)

(52) U.S. Cl.
   CPC ......... *G01N 21/6452* (2013.01); *G01N 21/94* (2013.01); *G01N 33/48792* (2013.01); *G01N 2021/6439* (2013.01)

(56) References Cited

U.S. PATENT DOCUMENTS

| | | | |
|---|---|---|---|
| 6,063,591 | A | 5/2000 | Bolea |
| 6,325,972 | B1 | 12/2001 | Jacobs et al. |
| 6,365,102 | B1 | 4/2002 | Wu et al. |
| 6,447,719 | B1 | 9/2002 | Agamohamadi et al. |
| 6,485,978 | B1 | 11/2002 | Kirckof et al. |
| 6,852,277 | B2 | 2/2005 | Platt et al. |
| 6,852,279 | B2 | 2/2005 | Williams et al. |
| 6,936,434 | B2 | 8/2005 | McDonnell et al. |
| 6,939,519 | B2 | 9/2005 | Agamohamadi et al. |
| 6,986,736 | B2 | 1/2006 | Williams et al. |
| 7,138,087 | B1 | 11/2006 | Malkin et al. |
| 7,479,257 | B2 | 1/2009 | Nguyen et al. |
| 7,686,761 | B2 | 3/2010 | Jackson et al. |
| 7,899,681 | B2 | 3/2011 | Katzenmaier et al. |
| 8,246,909 | B2 | 8/2012 | Williams et al. |
| 9,056,147 | B2 | 6/2015 | Ma |
| 9,068,976 | B2 | 6/2015 | Putnam et al. |
| 9,216,440 | B2 | 12/2015 | Ma et al. |
| 9,410,180 | B2 | 8/2016 | Pederson et al. |
| 10,201,269 | B2 | 2/2019 | Yang et al. |
| 10,443,083 | B2 | 10/2019 | Eghbal et al. |
| 10,561,753 | B2 | 2/2020 | Thompson et al. |
| 10,596,287 | B2 | 3/2020 | Dang et al. |
| 10,668,180 | B2 | 6/2020 | Thompson et al. |
| 2002/0009015 | A1 | 1/2002 | Laugharn et al. |
| 2003/0083902 | A1 | 5/2003 | Hehenberger et al. |
| 2003/0170901 | A1 | 9/2003 | Kippenhan et al. |
| 2004/0197848 | A1 | 10/2004 | Behun et al. |
| 2006/0263258 | A1* | 11/2006 | Harris ............... G01N 21/78 422/400 |
| 2013/0217107 | A1 | 8/2013 | Pederson et al. |
| 2013/0323117 | A1 | 12/2013 | Ma et al. |
| 2013/0323120 | A1 | 12/2013 | Ma |
| 2014/0053871 | A1 | 2/2014 | Ma et al. |
| 2014/0235975 | A1 | 8/2014 | Carnes |
| 2014/0264039 | A1 | 9/2014 | Kurkowski et al. |
| 2016/0235879 | A1* | 8/2016 | Andersson ............ A61L 2/24 |
| 2017/0252472 | A1 | 9/2017 | Dang et al. |
| 2017/0252473 | A1 | 9/2017 | Thompson et al. |
| 2017/0252474 | A1 | 9/2017 | Thompson et al. |
| 2017/0253845 | A1 | 9/2017 | Amin |
| 2017/0253905 | A1 | 9/2017 | Eghbal et al. |
| 2020/0179549 | A1 | 6/2020 | Thompson et al. |
| 2020/0330636 | A1 | 10/2020 | Thompson et al. |

FOREIGN PATENT DOCUMENTS

| | | |
|---|---|---|
| CN | 101095961 A | 1/2008 |
| CN | 101189519 A | 5/2008 |
| CN | 102245217 A | 11/2011 |
| CN | 102256631 A | 11/2011 |
| CN | 102364485 A | 2/2012 |
| CN | 102498218 A | 6/2012 |
| CN | 102740898 A | 10/2012 |
| CN | 103119173 A | 5/2013 |
| CN | 103201391 A | 7/2013 |
| CN | 103559572 A | 2/2014 |
| CN | 103606118 A | 2/2014 |
| CN | 104056292 A | 9/2014 |
| CN | 104380333 A | 2/2015 |
| CN | 104567982 A | 4/2015 |
| CN | 204671599 U | 9/2015 |
| CN | 105120906 A | 12/2015 |
| EP | 0629410 A1 | 12/1994 |
| EP | 1617878 A1 | 1/2006 |
| EP | 0981641 B1 | 5/2006 |
| EP | 2340853 A1 | 7/2011 |
| EP | 2792294 A1 | 10/2014 |
| JP | 2000-175995 A | 6/2000 |
| JP | 2000175995 A * | 6/2000 |
| JP | 2008-200126 A | 9/2008 |
| JP | 2009-095502 A | 5/2009 |
| JP | 2009-532090 A | 9/2009 |
| JP | 2010-119491 A | 6/2010 |
| JP | 2012-071029 A | 4/2012 |
| JP | 2012-105713 A | 6/2012 |
| JP | 2014-166209 A | 9/2014 |
| JP | 2014-179973 A | 9/2014 |
| KR | 2018-0038868 A | 4/2018 |
| RU | 2302000 C2 | 7/2007 |
| RU | 2522203 C2 | 7/2014 |
| WO | WO 96/25214 A1 | 8/1996 |
| WO | WO 2001/010475 A1 | 2/2001 |
| WO | WO 2004/093925 A1 | 11/2004 |
| WO | WO 2005/048041 A2 | 5/2005 |
| WO | WO 2006/086547 A2 | 8/2006 |
| WO | WO 2013/181393 A1 | 12/2013 |
| WO | WO 2014/159696 A1 | 10/2014 |
| WO | WO 2015/049002 A1 | 4/2015 |
| WO | WO 2015/080777 A1 | 6/2015 |

OTHER PUBLICATIONS

Japanese Notification of Reasons for Refusal dated Dec. 8, 2020 for Application No. 2017-038026, 4 pages.
Russian Office Action and Search Report dated Jun. 27, 2018 for Application No. 2017106748, 10 pages.
Chinese Office Action dated Dec. 25, 2020, for Application No. 201710120893.7, 17 pages.
Chinese Final Office Action dated Jan. 22, 2021, for Application No. 201710120892.2. 9 pages.
Chinese Office Action and Search report dated Apr. 14, 2020 for Application No. 201710120892.2, 13 pages.
Chinese Office Action and Search report dated May 7, 2020 for Application No. 201710120893.7, 16 pages.
U.S. Appl. No. 62/302,257, filed Mar. 2, 2016.
U.S. Appl. No. 62/316,722, filed Apr. 1, 2016.
U.S. Appl. No. 62/376,517, filed Aug. 18, 2016.
Tanaka, K., et al., "Evaluation of Perioperative Management Using Information Communication Technology—Construction of a Management System for Sterilization of Medical Instruments, Reservations System for Surgery, and Operation Workflow Management System—," Journal of the Japanese Society of Environmental Infections, 2008, 23(2):104-110, 10 pgs.
Noboru, K., "Sterilization indicator," Japanese Journal of Operating Room Nursing, Special Edition "The basics of sterilization that you should know now," Mar. 2003, (Sequential serial No. 227), 18(3):274-280. (Article not available, Bibliographic material attached. Please consider as prior art until proven otherwise.) 1 pg.
Chinese Search Report dated Jun. 11, 2021 for Application No. CN 201710120894.1, 1 pg.

(56) References Cited

OTHER PUBLICATIONS

Japanese Office Action, Notice of Reasons for Refusal, and First Search, dated Dec. 8, 2020 for Application No. JP 2017-038014, 18 pgs.
Japanese Search Report dated Oct. 23, 2020 for Application No. JP2017-038026, 32 pgs.
Japanese Office Action, Notice of Reasons for Refusal, dated Apr. 27, 2021 for Application No. JP 2017-038032, 5 pgs.
Chinese Office Action, The Second Office Action, dated Sep. 30, 2020 for Application No. CN 201710120892.2, 12 pgs.
Chinese Office Action, The First Office Action, and First Search Report dated Jul. 31, 2020 for Application No. CN 201710120894.1, 20 pgs.
European Examination Report dated Sep. 16, 2020 for Application No. EP 17158962.5, 4 pgs.
European Examination Report dated Sep. 16, 2020 for Application No. EP 17158975.7, 4 pgs.
Japanese Search Report dated Jul. 27, 2020 for Application No. JP 2017-038032, 159 pgs.
U.S. Appl. No. 16/868,683, filed May 7, 2020 by Thompson et al., entitled: "Apparatus and Method for Sterilizing Medical Devices."
Chinese Office Action and Search Report dated Jan. 5, 2021 for Application No. 201710120894.1, 10 pages.
European Search Report and Written Opinion, Extended, dated Jul. 27, 2017 for Application No. EP 17158975.7, 9 pages.
Extended European Search Report and Written Opinion dated Aug. 2, 2017 for Application No. 17158962.5, 8 pages.
European Search Report and Written Opinion, Partial, dated Aug. 1, 2017 for Application No. EP 17158813.0, 13 pages.
European Search Report and Written Opinion, Extended, dated Nov. 9, 2017 for Application No. EP 17158813.0, 11 pages.

\* cited by examiner

In-Progress Test Summary, Well No.6

Biological Indicator Info:

| | |
|---|---|
| Biological Indicator: | Test |
| Lot Number: | 123456-01 |
| Serial Number: | 987654321 |
| Expiration Date: | 01/2017 |
| Added By: | John Smith |
| Time Added: | 10:53 AM |
| Date: | 09/23/2015 |
| Chemical Indicator Color Change: | Yes |
| Temperature: | 60.0° C |

— 450

STERRAD Cycle Info:

| | |
|---|---|
| STERRAD ID: | 1-100NX 123456 |
| Cycle Type: | Standard |
| Cycle #: | 123 |
| Cycle Start Time: | 9:50 AM |
| Cycle End Time: | 10:40 AM |
| Cycle End Date: | 09/23/2015 |

◁ ▷

Done

Fig.16

APPARATUS AND METHOD FOR ANALYZING BIOLOGICAL INDICATORS

This application is a divisional of U.S. patent application Ser. No. 15/441,734, entitled "Apparatus and Method for Analyzing Biological Indicators," filed Feb. 24, 2017, and issued as U.S. Pat. No. 10,443,083 on Oct. 15, 2019.

PRIORITY

This application claims priority to U.S. Provisional Patent Application No. 62/302,257, entitled "System and Method for Sterilizing Medical Devices," filed Mar. 2, 2016, the disclosure of which is incorporated by reference herein.

This application also claims priority to U.S. Provisional Patent Application No. 62/316,722, entitled "System and Method for Sterilizing Medical Devices," filed Apr. 1, 2016, the disclosure of which is incorporated by reference herein.

This application also claims priority to U.S. Provisional Patent Application No. 62/376,517, entitled "Apparatus and Method to Link Medical Device Sterilization Equipment," filed Aug. 18, 2016, the disclosure of which is incorporated by reference herein.

BACKGROUND

Re-usable medical devices such as certain surgical instruments, endoscopes, etc., may be sterilized before re-use in order to minimize the likelihood that a contaminated device might be used on a patient, which could cause an infection in the patient. Various sterilization techniques may be employed, such as steam, hydrogen peroxide, and vapor phase sterilization, either with or without a gas plasma and ethylene oxide (EtO). Each of these methods may depend to a certain extent on the diffusion rates of the sterilization fluids (e.g., gases) upon the medical devices to be sterilized.

Before sterilization, medical devices may be packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device.

Although the packaging may help prevent contamination of a sterile medical device, the packaging may increase the difficulty of achieving a successful sterilization cycle because the packaging may impede the sterilant from reaching the medical device contained therein. This may be particularly problematic for medical devices that have diffusion-restricted spaces therein because these diffusion-restricted spaces may reduce the likelihood that a sterilization cycle may be effective. For example, some endoscopes have a long narrow lumen into which the sterilant must diffuse in sufficient concentration for sufficient time to achieve a successful sterilization cycle.

Sterilization of medical devices may be performed with an automated sterilization system such as a STERRAD® System by Advanced Sterilization Products of Irvine, Calif. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein; U.S. Pat. No. 6,852,279, entitled "Sterilization with Temperature-Controlled Diffusion Path," issued Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; and U.S. Pat. No. 6,447,719, entitled "Power System for Sterilization Systems Employing Low Frequency Plasma," issued Sep. 10, 2002, the disclosure of which is incorporated by reference herein. Medical devices must be carefully arranged and controlled within the sterilization system to maintain an environment that allows for effective sterilization. Each different medical device may require a different arrangement and sterilization process, meaning that use of a sterilization system can still be error prone and may heavily rely upon operator training and knowledge, or related documentation.

In addition, re-use of the same sterilizing chamber of a sterilization system may result in cross contamination, particularly when the sterilization system is not operated correctly. Operator error may result in medical devices that are erroneously believed to be decontaminated being returned to service. Confirming that a sterilization cycle has been efficacious may help medical personnel avoid using a contaminated medical device on a patient. The sterilized medical device might not itself be checked for contaminating organisms because such an activity may introduce other contaminating organisms to the medical device, thereby re-contaminating it. Thus, an indirect check may be performed using a sterilization indicator. A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms may be placed into a sterilization chamber alongside a medical device and subject to a sterilization cycle. After the cycle is complete, the microorganisms in the biological indicator may be cultured to determine whether any of the microorganisms survived the cycle.

In view of the foregoing, it may be desirable to provide a sterilization system that minimizes opportunities for operator error, thereby maximizing the likelihood of successful sterilization cycles, thereby minimizing the risk of patient infection. While a variety of systems and methods have been made and used for surgical instrument sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 16 depicts a screenshot of an exemplary user interface that could be presented via a display of the indicator analyzer of FIG. 4 to provide a detailed status of an indicator during incubation and analysis;

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Sterilization System and Devices

Figure 1:
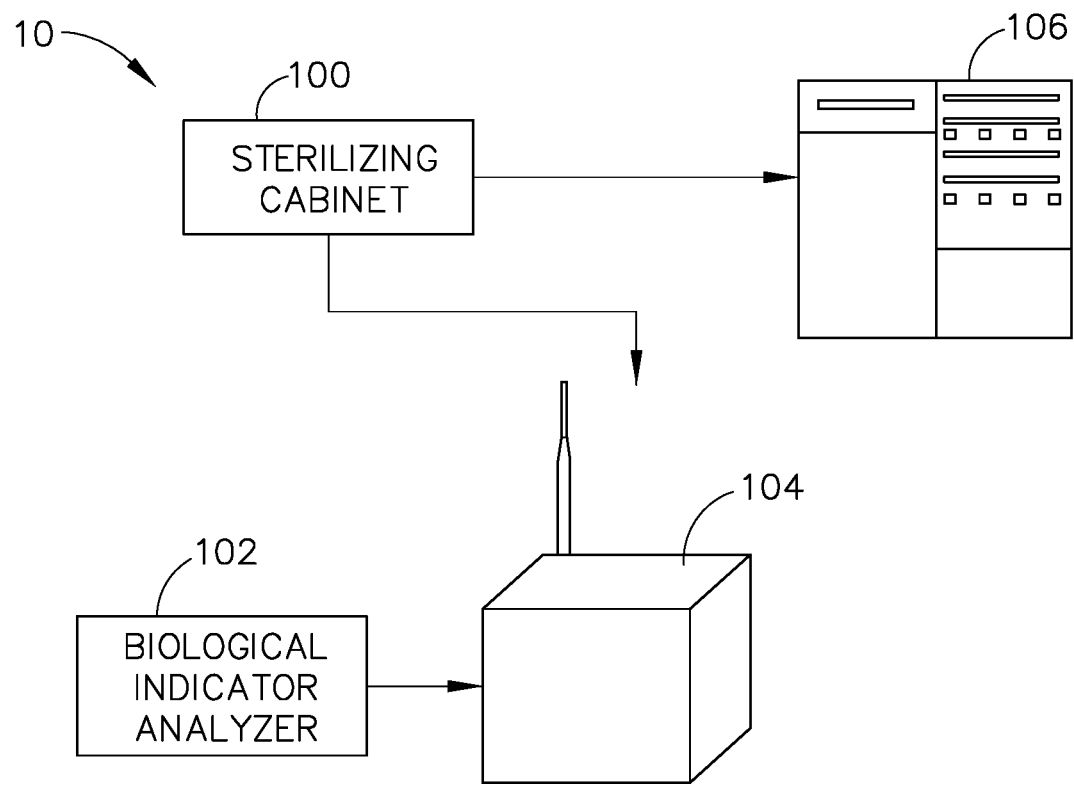
FIG. 1 depicts a schematic view of an exemplary sterilization system.

FIG. 1 depicts a schematic view of an exemplary system (10) of interconnected devices that may be configured to perform methods for sterilizing medical devices. System (10) of this example includes a sterilizing cabinet (100), a biological indicator analyzer (102), a communication hub (104), and a server (106). In the present example, sterilizing cabinet (100) includes a sterilization chamber, which is configured to receive one or more medical devices for sterilization. Sterilizing cabinet (100) also includes a door that opens and closes a sterilization chamber in response to actuation of a kick plate. An operator may thereby open and close the sterilization chamber in a hands-free fashion. Sterilizing cabinet (100) also includes a sterilization module that is operable to dispense a sterilant into the sterilization chamber in order to sterilize medical devices contained in the sterilization chamber. In the present example, the sterilization module is configured to receive replaceable sterilant cartridges containing a certain amount of sterilant.

Sterilizing cabinet (100) of the present example further includes a touch screen display. The touch screen display is operable to render the various user interface display screens. The touch screen display is further configured to receive user input in the form of the user contacting the touch screen display in accordance with conventional touch screen technology. Sterilizing cabinet (100) of the present example further includes a communication module. The communication module is configured to enable bidirectional communication between sterilizing cabinet (100) and communication hub (104). In addition, or in the alternative, the communication module may be configured to enable bidirectional communication between sterilizing cabinet (100) and server (106).

Sterilizing cabinet (100) of the present example further includes a reader, which is operable to read an identification tag of a biological indicator as described herein. By way of example only, the reader may comprise an optical reader that is operable to read an optical identification tag (e.g., barcode, QR code, etc.) of a biological indicator. In addition or in the alternative, the reader may comprise RFID reader that is operable to read an RFID identification tag (e.g., barcode, QR code, etc.) of a biological indicator. Various suitable components and configurations that may be used to form the reader will be apparent to those of ordinary skill in the art in view of the teachings herein. Data received through the reader is processed through the processor.

In addition to the foregoing, sterilizing cabinet (100) may be configured and operable in accordance with at least some of the teachings of any of the U.S. provisional patent applications cited herein, U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; and/or U.S. Pat. No. 6,447,719, the disclosure of which is incorporated by reference herein.

Server (106) may include a hospital record server or hospital local area network server. Server (106) may receive information from sterilizing cabinet (100) relating to sterilization procedures performed by the sterilizing cabinet (100), such as sterilization procedure durations and results; whether a particular sterilization procedure provided a subsequent indication of biological contamination; the identification of a user or technician who initiated, canceled, or complete a sterilization procedure; consumable materials or supplies used during a sterilization procedure; diagnostic information and systems errors; and/or other information. Server (106) may also provide information to the sterilizing cabinet (100) such as software updates, configuration updates, user authentication information, biological indicator use protocols, and other information. Communication between sterilizing cabinet (100) and server (106) may be accomplished via any suitable wired and/or wireless communication technology, such as Ethernet, Wi-Fi, Bluetooth, USB, infrared, NFC, and/or other technologies.

In system (10) of the present example, sterilizing cabinet (100) is also in communication with a communication hub (104), which itself is in communication with one or more biological indicator analyzers (102). As will be described in greater detail below, biological indicator analyzer (102) may comprise a desktop or wall mounted device that receives a biological indicator and measures one or more characteristics of the biological indicator in order to gather data that may be used to determine whether the biological indicator tests positive, indicating that contamination is present after a sterilization procedure; or negative, indicating that no contamination is present after the sterilization procedure.

In some versions, biological indicator analyzer (102) will measure and transmit data to communication hub (104), which will process the data to determine if there is contamination. In other versions, biological indicator analyzer (102) itself may both measure and analyze the data to determine whether there is contamination, and communication hub (104) may be used to receive, gather, and transmit such information to sterilizing cabinet (100) and/or other devices as will be described in greater detail below. In still other versions, biological indicator analyzer (102) and communication hub (104) may be different components of a single device; or may be components of sterilizing cabinet (100). Such variations may be desirable depending upon a particular implementation environment and user needs, such that a single device incorporating sterilizing cabinet (100), communication hub (104), and biological indicator analyzer (102) may be desirable in a semi-portable unit; while an implementation supporting a one-to-many relationship between sterilizing cabinet (100) and biological indicator analyzer (102) may be more advantageous for permanent installation in a large hospital with many users.

After receiving data from biological indicator analyzer (102) identifying sterilization cycles whose success may be questionable, and thus medical devices whose sterility may be questionable, communication hub (104) may automatically send out notifications to various other devices in order to prevent such medical devices from being used before being put through another sterilization process. By way of example only, communication hub (104) may push a notification to sterilizing cabinet (100) indicating the sterilization cycles whose success may be questionable, and thus medical devices whose sterility may be questionable. Sterilizing cabinet (100) may relay this notification to a user. In addition or in the alternative, communication hub (104) may push a notification to server (106) indicating the sterilization cycles whose success may be questionable, and thus medical devices whose sterility may be questionable. Of course, communication hub (104) may also push a notification to server (106) indicating when a biological indicator passed analysis and/or other information associated with operation of sterilizing cabinet (100) and/or biological indicator analyzer (102).

In addition or in the alternative, communication hub (104) may push a notification to one or more mobile devices, such as an operator of system (10), etc., indicating the sterilization cycles whose success may be questionable, and thus medical devices whose sterility may be questionable. In some versions, communication hub (104) pushes such notifications to a mobile device associated with a person who was identified as a user of sterilizing cabinet (100) and/or a person who was identified as a user of biological indicator analyzer (102). Of course, communication hub (104) may also push a notification to one or more mobile devices indicating when a biological indicator passed analysis and/or other information associated with operation of sterilizing cabinet (100) and/or biological indicator analyzer (102).

Biological indicator analyzer (102) and sterilizing cabinet (100) may each be coupled with communication hub (104) via any suitable wired and/or wireless communication technology, such as Ethernet, Wi-Fi, Bluetooth, USB, infrared, NFC, and/or other technologies. It should also be understood that communication hub (104) may be in communication with various other components, via wire or wirelessly, including but not limited to desktop computers, laptop computers, mobile computing devices, smartphones, etc. Moreover, communication hub (104) may be in communication with server (106) via wire or wirelessly. In versions where communication hub (104) is in communication with server (106), communication hub (104) may relay data, etc., between sterilizing cabinet (100) and server (106), such that communication hub (104) serves as an intermediary between sterilizing cabinet (100) and server (106). It should therefore be understood that, in some versions, sterilizing cabinet (100) may be in communication with server (106) via communication hub (104) instead of being directly in communication with server (106).

By way of example only, communication hub (104) may be constructed and operable in accordance with at least some of the teachings of U.S. Provisional Patent Application No. 62/376,517, entitled "Apparatus and Method to Link Medical Device Sterilization Equipment," filed Aug. 18, 2016, the disclosure of which is incorporated by reference herein. Various suitable components and configurations that may be used to form communication hub (104) will be apparent to those of ordinary skill in the art in view of the teachings herein.

II. Exemplary Sterilization Processes and Interfaces

Figure 2:
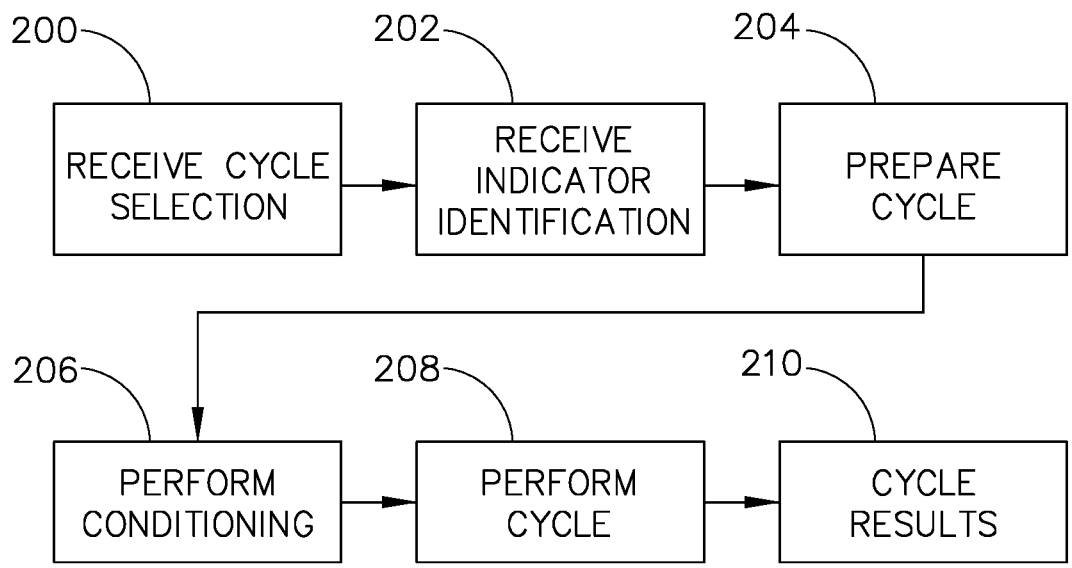
FIG. 2 depicts a high level flowchart of an exemplary set of steps that a sterilizing cabinet of the system of FIG. 1 could perform to sterilize a medical device.

FIG. 2 depicts a high level flowchart of an exemplary set of steps that system (10) could perform to sterilize a medical device. A user may interact with the system via a user interface such as a keyboard or touch screen of sterilizing cabinet (100), as will be described in greater detail below; or via an input device in communication with sterilizing cabinet (100). Initially, sterilizing cabinet (100) may display one or more sterilization cycles via a display and then receive a sterilization cycle selection (block 200) from the user. Sterilizing cabinet (100) may be configured to perform one or more sterilization cycles, with different sterilization cycles being appropriate for different types and quantities of medical devices.

Sterilizing cabinet (100) may also display instructions indicating whether a biological indicator should be used with the selected sterilization cycle, and receive a biological indicator identification (block 202). A biological indicator may be placed inside a sterilization chamber of sterilizing cabinet (100) before the sterilization cycle begins and may remain in the sterilization chamber during a sterilization cycle. The user may thus identify the particular biological indicator (block 202) before the biological indicator is placed in the sterilization chamber. The biological indicator may contain microorganisms that are responsive to a particular sterilization cycle. Upon completion of the sterilization cycle, the biological indicator may be tested for the microorganisms in order to provide a measure of the effectiveness of the sterilization cycle. A biological indicator may not necessarily be required for all sterilization cycles, but may be required based on hospital rules or local regulations. When used, a biological indicator may be identified by manual input, such as keyboard entry of a biological indicator type or identifier; or may be identified automatically, such as by an optical scan of an optical identifier or a wireless scan of an RFID or other unique identifier.

Selection of a sterilization cycle (block 200) and identification of a biological indicator (block 202) may define one or more requirements for the configuration and arrangement of medical devices within sterilizing cabinet (100). A door of the sterilization chamber of sterilizing cabinet (100) may be opened and instructions may be displayed to guide a user through preparation of the sterilization cycle (block 204), including placement of the biological indicator, placement of medical devices, closing the door of the sterilization chamber of the sterilization cabinet (100), and/or other changes in preparation. Before initiating the actual sterilization cycle (block 208), sterilization cabinet (100) may also perform load conditioning (block 206) of the medical devices that are loaded in the sterilization chamber of the sterilization cabinet (100). Such load conditioning (block 206) may include verifying that the sterilization chamber is sealed; verifying contents of the sterilization chamber; checking physical characteristics of the contents of the sterilization chamber such as moisture levels, content volume, content weight, internal temperature, or other characteristics; and/or performing one or more conditioning steps that may include heat treatment, chemical treatment, plasma treatment, or other types of treatment to reduce moisture, raise temperature, and/or otherwise prepare the medical devices in the sterilization chamber for the sterilization cycle.

Once the load conditioning (block 206) has been completed, the selected sterilization cycle itself may be performed (block 208). The sterilization cycle (block 208) may include exposing the medical device(s) in the sterilizing chamber to pressurized sterilant gas, further heat treatment, chemical treatment, plasma treatment, vacuum treatment, and/or other types of sterilization procedures. After the sterilization cycle (block 208) is completed, the complete sterilization results may be displayed to a user via a display of the sterilization cabinet; transmitted to server (106); printed locally; and/or displayed, transmitted, and/or stored via other devices as may be desirable.

Sterilization cabinet (100) may also provide results (block 210) of the sterilization cycle. This provision of results (block 210) may include results from analysis of a biological indicator via biological indicator analyzer (102) as described below. These results may include a positive or negative indication of contamination present in the biological indicator at the completion of the sterilization cycle (block 208). In cases where the biological indicator suggests that contamination is present after completion of the sterilization cycle (block 208), additional actions may be taken such as alerting a user of the positive test and analysis of sterilization cycle history in order to determine if other past cycles may be the cause of the contamination; and/or if subsequently sterilized medical devices may need to be re-sterilized.

III. Exemplary Biological Indicator Assembly

Figure 3:
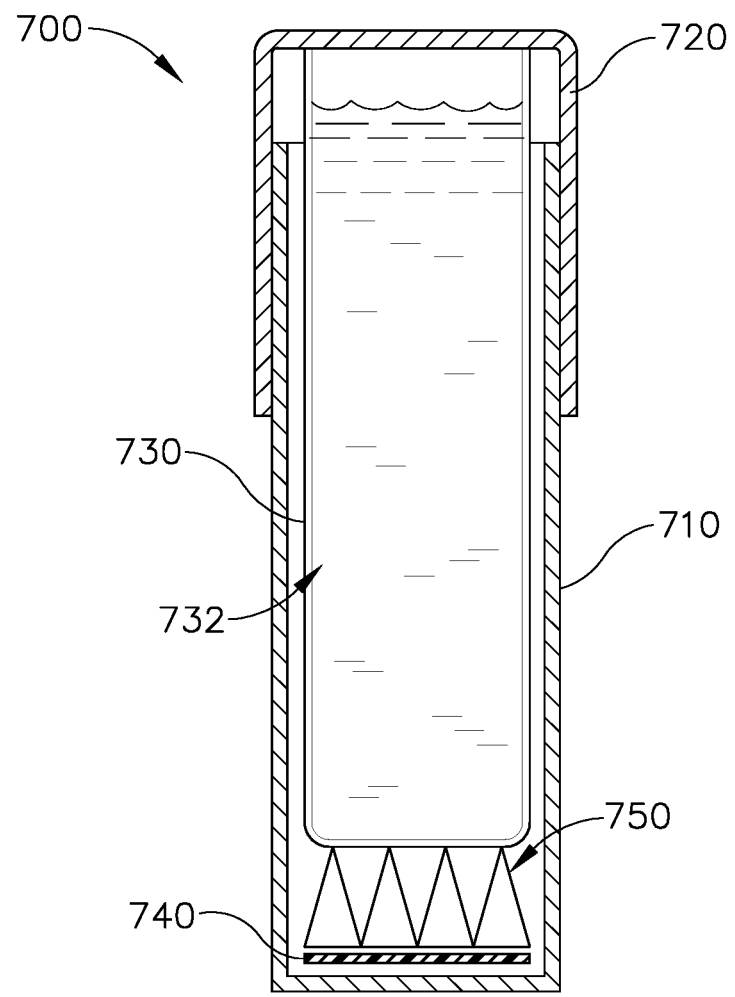
FIG. 3 depicts a schematic view of an exemplary biological indicator assembly that may be used with the system of FIG. 1.

As noted above, a biological indicator may be included in sterilizing cabinet (100) along with the medical device during the sterilization process (block 208) in order to ensure that the sterilization process (block 208) was successful. FIG. 3 shows an exemplary form that such a biological indicator may take. In particular, FIG. 3 shows a biological indicator (700) that includes a housing (710), a cap (720), an ampoule (730), and a carrier (740). Housing (710) is formed of a transparent material (e.g., clear plastic, glass, etc.) and is hollow such that housing (710) insertably receives ampoule (730). Ampoule (730) is also formed of a transparent material (e.g., clear plastic, glass, etc.) and contains a fluid (732). By way of example only, fluid (732) may comprise a liquid growth medium. Such a liquid growth medium is capable of, with incubation, promoting growth of any viable microorganisms it contacts. Fluid (732) also includes a fluorophore whose fluorescence depends on the amount of microorganisms contained in the medium. Fluid (732) is sealed within ampoule (730).

Carrier (740) provides a source of microorganisms or active enzymes. By way of example only, carrier (740) may be impregnated with bacterial spores, other forms of bacteria (e.g., vegetative), and/or active enzymes. By way of example only, spores from *Bacillus*, *Geobacillus*, and *Clostridium* species may be used. Carrier (740) may be water-absorbent and may be formed of filter paper. Sheet-like materials such as cloth, nonwoven polypropylene, rayon or nylon, and microporous polymeric materials may also be used to form carrier (740). Non-water absorbent materials may also be used to form carrier (740), such as metals (e.g., aluminum or stainless steel), glass (e.g., glass beads or glass fibers), porcelain, or plastic. Of course, combinations of the foregoing materials may also be used to form carrier (740).

Ampoule (730) is configured as a frangible component of biological indicator (700), such that ampoule (730) may be fractured within housing to release fluid (732) in housing (710). To assist in the fracture of ampoule (730), a set of fracturing features (750) are disposed in the bottom of housing (710). While fracturing features (750) are shown as spikes in FIG. 3, it should be understood that this is merely illustrative. Fracturing features (750) may take any other suitable form. To further assist in the fracture of ampoule (730), cap (720) is configured to slide downwardly along housing (710) to press ampoule (730) against fracturing features (750). This may be done right before biological indicator (700) is inserted into indicator analyzer (102, 800) as described in greater detail below. It should be understood that ampoule (730) would remain intact while biological indicator (700) is in sterilizing cabinet (100) during a sterilization process.

Cap (720) may include one or more openings that allow gasses (e.g., air or sterilant, etc.) to pass into housing (710)

before cap (720) is pressed downwardly relative to housing (710) to fracture ampoule (730). These openings may thus enable the microorganisms on carrier (740) to be destroyed by the sterilization process (block 208). However, after cap (720) is pressed downwardly relative to housing (710) to fracture ampoule (730), these one or more openings may be sealed to contain the released fluid (732) in housing (710). When fluid (732) is released from ampoule (730), the released fluid eventually reaches carrier (740), thereby initiating an incubation process with any living microorganisms remaining on carrier (740), as will be described in greater detail below.

While not shown in FIG. 3, housing (710) may also include an identification tag. Such an identification tag may include a machine readable feature that is capable of being read by the reader of sterilizing cabinet (100) and indicator analyzer (102). In other words, the identification tag may be read perform to the steps of indicator scanning (block 302, block 308) described above with reference to FIG. 3. By way of example only, the identification tag may comprise an optical code (e.g., a barcode, a QR code, etc.), an RFID tag, and/or any other suitable kind of machine readable identifier. In addition, the identification tag may include human readable features such as text, numbers, color coding, etc.

Cap (720) may also include a color changing feature. Such a color changing feature may serve as a chemical indicator that changes color when biological indicator (700) is exposed to the sterilant of sterilizing cabinet (100). In some versions, the color changing feature simply changes between two distinctive colors, with one of the colors indicating no exposure to a sterilant and the other color indicating at least some exposure to a sterilant. In some other versions, the color changing feature changes along a range of colors based on the extent to which biological indicator (700) has been exposed to a sterilant. In other words, the color change may be proportional to the degree of sterilant exposure.

In addition to or in lieu of the foregoing, biological indicator (700) may be configured and operable in accordance with at least some of the teachings of U.S. patent application Ser. No. 15/057,768, entitled "Self-Contained Biological Indicator," filed Mar. 1, 2016, the disclosure of which is incorporated by reference herein. Other suitable forms that biological indicator (700) may take will be apparent to those of ordinary skill in the art in view of the teachings herein.

IV. Exemplary Biological Indicator Analyzer

A. Exemplary Biological Indicator Analyzer Hardware

Figure 4:
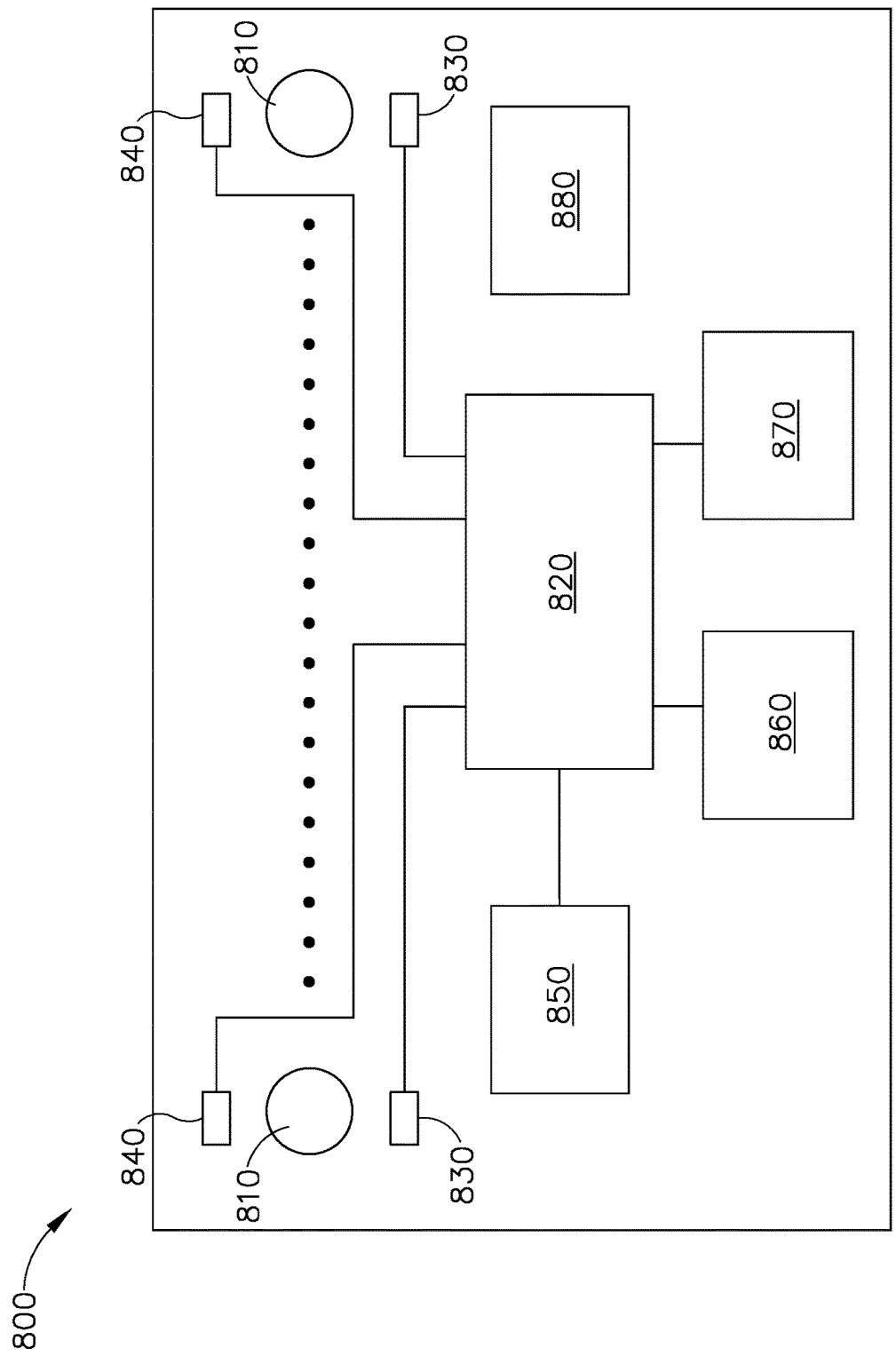
FIG. 4 depicts a schematic view of an exemplary indicator analyzer that may be used to process the biological indicator assembly of FIG. 3 as part of the system of FIG. 1.

FIG. 4 depicts an exemplary set of components that may be incorporated into biological indicator analyzer (102). Biological indicator analyzer (800) of this example comprises a plurality of wells (810), each of which is configured to insertingly receive a respective biological indicator (700). While two wells (810) are shown, it should be understood that any other suitable number of wells (810) may be provided, including eight wells (810), less than eight wells (810), or more than eight wells (810). Biological indicator analyzer (800) also includes a processor (820) that is operable to execute instructions and control algorithms, process information, etc.

Each well (810) has an associated light source (830) and sensor (840). Each light source (830) is configured to project light through housing (710) of the biological indicator (700) that is inserted in the corresponding well (810); and each sensor (840) is operable to detect light fluoresced by fluid (732) contained in housing (710). By way of example only, light source (830) may be in the form of a laser that is configured to emit ultraviolet light. Various other suitable forms that light source (830) may take will be apparent to those of ordinary skill in the art in view of the teachings herein. By way of further example only, sensor (840) may comprise a charge coupled device (CCD). Various other suitable forms that sensor (840) may take will be apparent to those of ordinary skill in the art in view of the teachings herein. As noted above, the fluorescence of fluid (732) will depend on the amount of living microorganisms contained in the medium of fluid (732). Thus, sensor (840) will be able to detect the presence of living microorganisms in fluid (732) based on the degree to which fluid (732) fluoresces in response to light from light source (830).

Biological indicator analyzer (800) of the present example further includes a touch screen display (850). Touch screen display (850) is operable to render various user interface display screens associated with operation of biological indicator analyzer (800). Touch screen display (850) is further configured to receive user input in the form of the user contacting touch screen display (850) in accordance with conventional touch screen technology. In addition or in the alternative, biological indicator analyzer (800) may include various other kinds of user input features, including but not limited to buttons, keypads, keyboards, a mouse, a trackball, etc. Displays provided through touch screen display (850) may be driven by processor (820). User inputs received through touch screen display (850) may be processed by processor (820).

Biological indicator analyzer (800) of the present example further includes a communication module (860). Communication module (860) is configured to enable bidirectional communication between biological indicator analyzer (800) and communication hub (104). In addition or in the alternative, communication module may be configured to enable bidirectional communication between biological indicator analyzer (800) and server (106). By way of example only, communication module (860) may be configured to provide wired and/or wireless communication via as Ethernet, Wi-Fi, Bluetooth, USB, infrared, NFC, and/or other technologies. Various suitable components and configurations that may be used to form communication module (860) will be apparent to those of ordinary skill in the art in view of the teachings herein. Communications that are sent from or received through communication module (860) are processed through processor (820).

Biological indicator analyzer (800) of the present example further includes a reader (870), which is operable to read an identification tag of biological indicator (700) as described herein. It should be understood that reader (870) may be used to identify biological indicator (700) before biological indicator (700) is analyzed (block 512). By way of example only, reader (870) may comprise an optical reader that is operable to read an optical identification tag (e.g., barcode, QR code, etc.) of a biological indicator. In addition or in the alternative, reader (870) may comprise RFID reader that is operable to read an RFID identification tag (e.g., barcode, QR code, etc.) of a biological indicator. Various suitable components and configurations that may be used to form reader (870) will be apparent to those of ordinary skill in the art in view of the teachings herein. Data received through reader (870) is processed through processor (820).

Biological indicator analyzer (800) of the present example further includes a memory (880), which is operable to store control logic and instructions and that are executed by processor (820) to drive components such as light source (830), touch screen display (850), communication module (860), and reader (870). Memory (880) may also be used to store results associated with performance of biological indicator analysis, and/or various other kinds of information. Various suitable forms that memory (880) may take, as well as various ways in which memory (880) may be used, will be apparent to those of ordinary skill in the art in view of the teachings herein.

Figure 5:
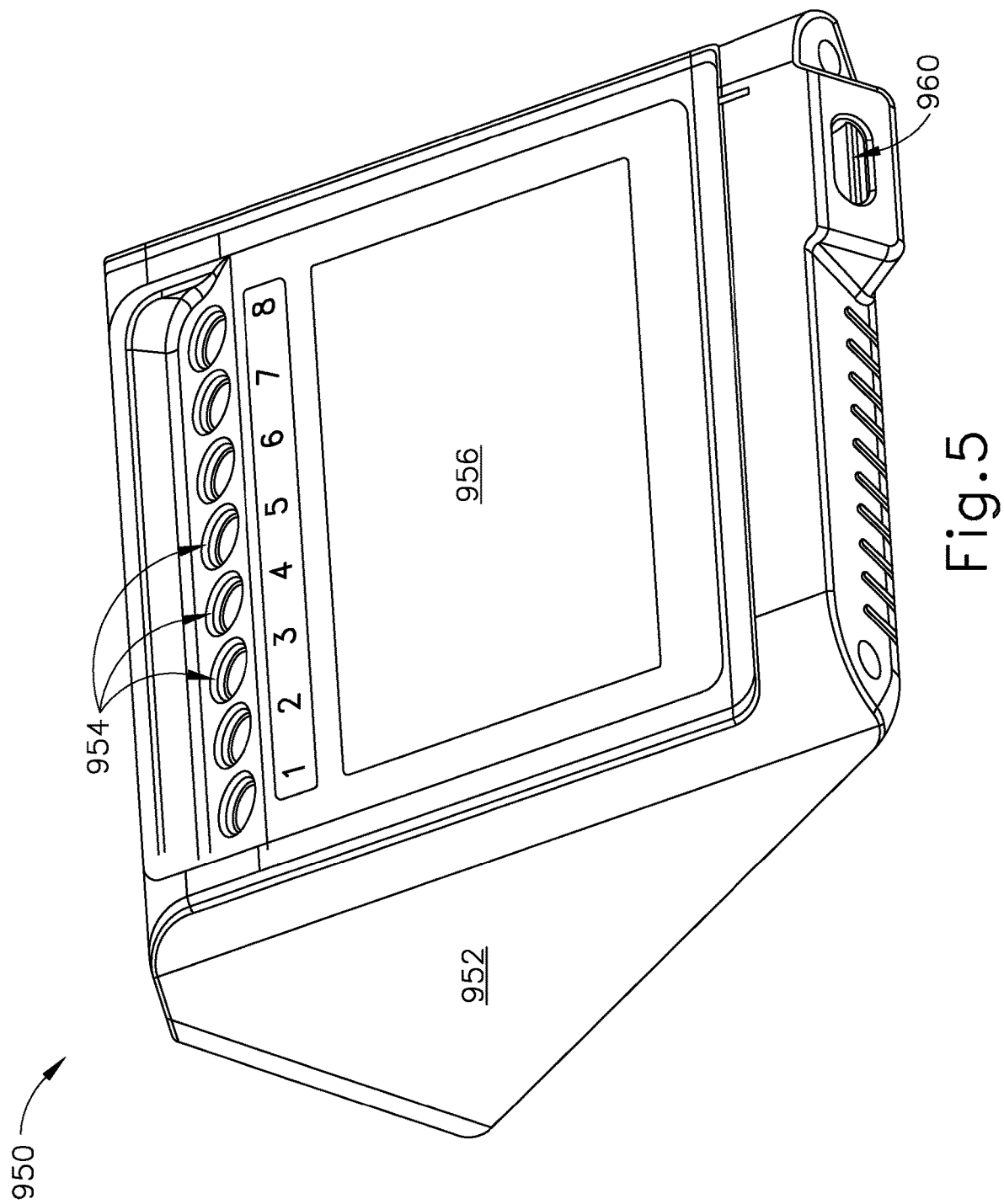
FIG. 5 depicts a perspective view of an exemplary form that the indicator analyzer of FIG. 4 may take.

FIG. 5 shows an exemplary form that indicator analyzer (800) may take. In particular, FIG. 5 shows an indicator analyzer (950) that includes a housing (952) with a set of eight wells (954), a touch screen display (956), and a reader (960). Housing (952) is configured to sit on a tabletop or other horizontal surface and present touch screen (956) at an oblique angle relative to the surface upon which housing (952) rests. Wells (954) are configured and operable like wells (810) described above. Touch screen display (956) is configured and operable like touch screen display (850) described above. Various examples of interactive screens that may be displayed via touch screen displays (850, 956) will be described in greater detail below. Reader (960) is configured and operable like reader (870) described above. It should be understood that indicator analyzer (950) may further include the other features described above with respect to indicator analyzer (800); and may further provide the same functionality and operability described above with respect to indicator analyzer (800). Other suitable forms that indicator analyzer (102, 800, 950) may take will be apparent to those of ordinary skill in the art in view of the teachings herein.

B. Exemplary Biological Indicator Processes and Interfaces

Figure 6:
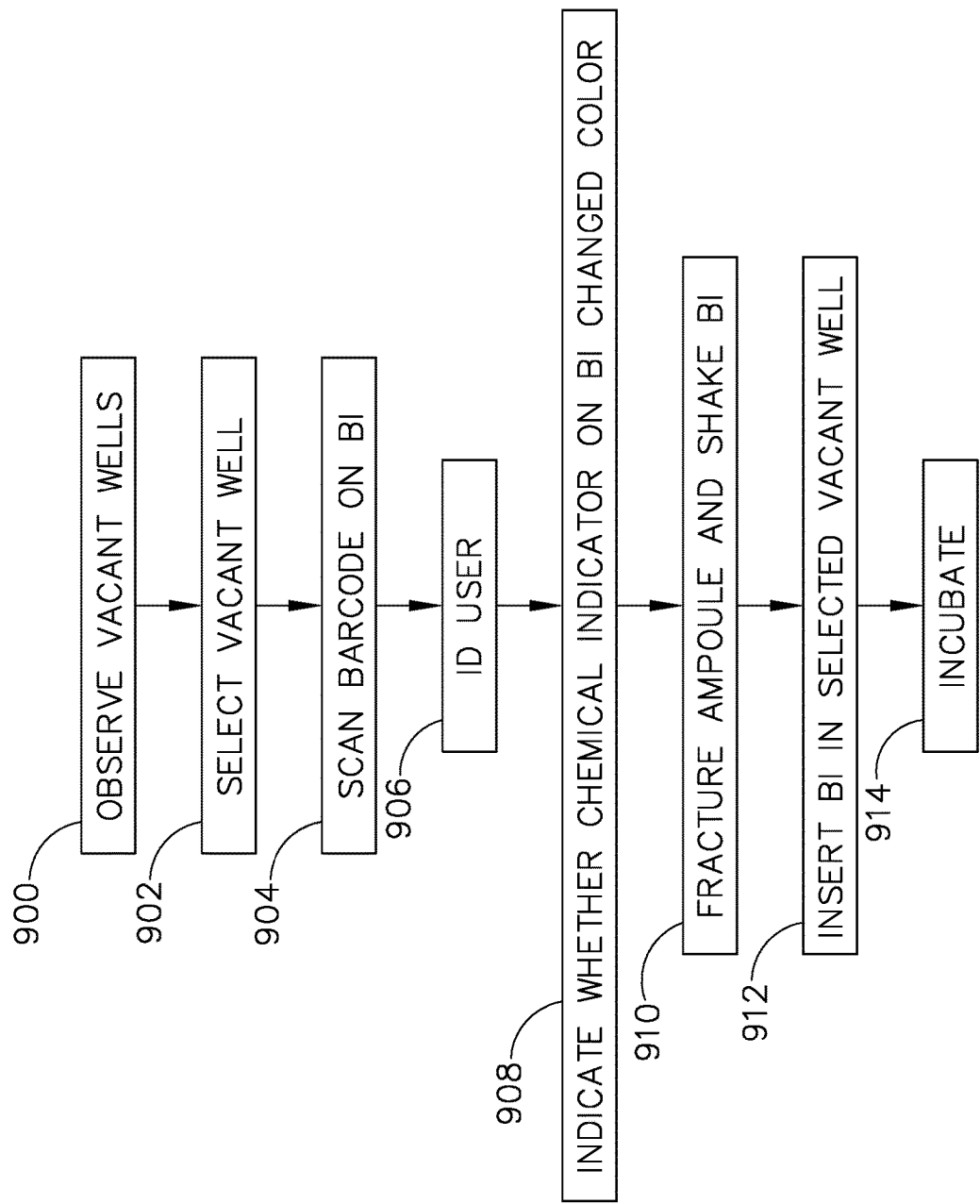
FIG. 6 depicts a flowchart of exemplary steps that may be performed by the indicator analyzer of FIG. 4 in preparation for analysis of the biological indicator assembly of FIG. 3.

FIG. 6 shows an exemplary set of steps that may be used to initiate biological indicator (700) analysis cycle by biological indicator analyzer (102, 800, 950). As a first step, the user may observe which wells (810, 954) are vacant (block 900) and select a vacant well (block 902). In some versions, touch screen display (850, 956) presents a number next to each vacant well (810, 954), such that the operator simply touches the number associated with the selected vacant well (810, 954) in order to effect selection of that vacant well (block 902). Next, a display screen on touch screen display (850, 956) may prompt the user to place the identification tag of biological indicator (700) near reader (870, 960) to enable reader (870, 960) to read the identification tag of biological indicator (700). As part of this prompting, touch screen display (850, 956) may point to the location of reader (870, 960) to assist the user in finding reader (870, 960). The user may then use reader (870, 960) to read the identification tag of biological indicator (700) (block 904).

A display screen on touch screen display (850, 956) may then prompt the user to identify himself or herself. The user may then manipulate touch screen display (850, 956) to identify himself or herself (block 906). A display screen on touch screen display (850, 956) may then prompt the user to indicate whether the chemical indicator on cap (720) of biological indicator (700) has changed color. The user may then manipulate touch screen display (850, 956) to indicate whether the chemical indicator on cap (720) of biological indicator (700) has changed color (block 908).

A display screen on touch screen display (850, 956) may then prompt the user to prepare biological indicator (700) for loading into the selected well (810, 954) by fracturing ampoule (730) and shaking biological indicator (700). The operator may then fracture ampoule (730) by pressing on cap (720), then shake biological indicator (700) (block 910) to ensure proper mixing of fluid (732) with carrier (740). The user may then quickly place biological indicator (700) in the selected well (810, 954) (block 912). In some instances it may be desirable to insert biological indicator (700) in the selected well (810, 954) (block 912) immediately after fracturing ampoule (730) and shaking biological indicator (700) (block 910).

In some versions, indicator analyzer (102, 800, 950) is configured to determine whether the user appropriately completed the step of fracturing ampoule (730) and shaking biological indicator (700) (block 910) before inserting biological indicator (700) in the selected well (810, 954) (block 912). By way of example only, this may be determined based on how sensor (840) detects light emitted by light source (830) after biological indicator (700) is inserted in the selected well (810, 954). In the event that indicator analyzer (102, 800, 950) determines that the user failed to appropriately complete the step of fracturing ampoule (730) and shaking biological indicator (700) (block 910) before inserting biological indicator (700) in the selected well (810, 954) (block 912), touch screen display (850, 956) may prompt the user to withdraw biological indicator (700) from well (810, 954) and properly complete the step of fracturing ampoule (730) and shaking biological indicator (700) (block 910).

To the extent that the user has properly completed the step of fracturing ampoule (730) and shaking biological indicator (700) (block 910), and then inserted biological indicator (700) in the selected well (block 912), biological indicator (700) is allowed to sit in well (810, 954) for an incubation period (block 914). During the incubation period (block 914), light source (830) associated with the selected well (810, 954) is activated and sensor (840) monitors responsive fluorescence of fluid (732) in indicator (700). Well (810, 954) may also be heated (e.g., to approximately 60° C.) during the incubation period (block 914). As noted above, fluid (732) includes a fluorophore whose fluorescence depends on the amount of microorganisms contained in the medium. Thus, sensor (8400 can detect the presence of living microorganisms (from carrier (740)) in fluid (732) based on the fluorescence of fluid (732). It should therefore be understood that, after a suitable incubation period has passed, indicator analyzer (102, 800, 950) will conclude whether any of the microorganisms that were on carrier (740) (i.e., before the sterilization cycle in sterilization cabinet (100)) survived the sterilization cycle in sterilization cabinet (100), based on the fluorescence of fluid (732) as sensed by sensor (840).

By way of example only, the incubation period (block 914) may be approximately 30 minutes. Alternatively, the incubation period may be substantially longer (e.g., one or more hours), shorter, or of any other suitable duration. During the incubation period (block 914), touch screen display (850, 956) may provide a graphical representation of the amount of time remaining in the incubation period. When more than one well (810, 954) is occupied by a corresponding biological indicator (700), touch screen display (850, 956) may provide a graphical representation of the amount of time remaining in the incubation period for each occupied well (810, 954).

Figures 7, 8:
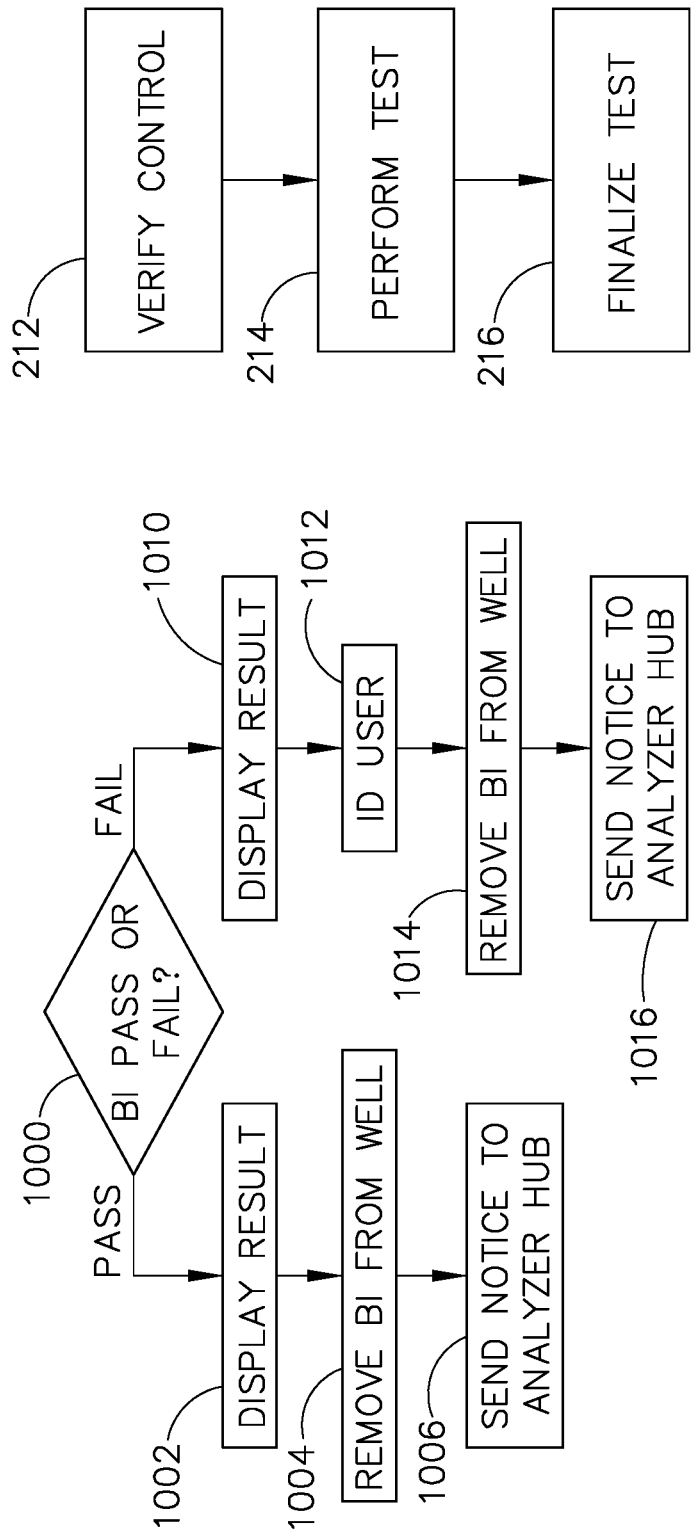
FIG. 7 depicts a flowchart of exemplary steps that may be performed by the indicator analyzer of FIG. 4 based on whether the biological indicator assembly of FIG. 3 passes or fails analysis.
FIG. 8 depicts a high level flowchart of exemplary steps that may be performed by the indicator analyzer of FIG. 4 to provide results for a biological indicator.

FIG. 7 shows a set of exemplary steps that may be carried out once the incubation period (block 914) is complete. As noted above, biological indicator analyzer (102, 800, 950) can determine whether any of the microorganisms that were on carrier (740) (i.e., before the sterilization cycle in sterilization cabinet (100)) survived the sterilization cycle in sterilization cabinet (100), based on the fluorescence of fluid (732) as sensed by sensor (840). Thus, biological indicator analyzer (102, 800, 950) can determine whether biological indicator (700) passes or fails analysis (block 1000). In this sense, a "pass" result indicates that no living microorganisms are present in biological indicator (700), which indicates that the sterilization cycle (block 208) in sterilization cabinet (100) was successful. A "fail" result indicates that living microorganisms are present in biological indicator (700), which indicates that the sterilization cycle (block 208) in sterilization cabinet (100) was unsuccessful.

In the event of a "pass" result, touch screen display (850, 956) may present a screen to the user indicating that biological indicator (700) passed the analysis (block 1002). Touch screen display (850, 956) may also prompt the user to remove biological indicator (700) from well (810, 954) (block 1004) and appropriately discard the used biological indicator (700). As described in greater detail below, biological indicator analyzer (102, 800, 950) may also transmit the "pass" result (and associated data) to communication hub (104) (block 1006) via communication module (860). In some versions, this transmission of the "pass" result (and associated data) to communication hub (104) (block 1006) is done in response to a query from communication hub (104), such that the "pass" result (and associated data) is pulled from biological indicator analyzer (102, 800, 950) by communication hub (104). In some other versions, the "pass" result (and associated data) is pushed to communication hub (104) (block 1006) by biological indicator analyzer (102, 800, 950), without requiring a query from communication hub (104).

In the event of a "fail" result, touch screen display (850, 956) may present a screen to the user indicating that biological indicator (700) failed the analysis (block 1010). Touch screen display (850, 956) may then prompt the user to identify himself or herself. The user may then manipulate touch screen display (850, 956) to identify himself or herself (block 1012). Touch screen display (850, 956) may then prompt the user to remove biological indicator (700) from well (810, 954) (block 1014) and appropriately discard the used biological indicator (700). As described in greater detail below, biological indicator analyzer (102, 800, 950) may also transmit the "fail" result (and associated data) to communication hub (104) (block 1016) via communication module (860). In some versions, this transmission of the "fail" result (and associated data) to communication hub (104) (block 1016) is done in response to a query from communication hub (104), such that the "fail" result (and associated data) is pulled from biological indicator analyzer (102, 800, 950) by communication hub (104). In some other versions, the "fail" result (and associated data) is pushed to communication hub (104) (block 1016) by biological indicator analyzer (102, 800, 950), without requiring a query from communication hub (104).

FIG. 8 shows a set of exemplary high level steps that may be performed by an indicator analyzer (102, 800, 950) to employ the use of an experimental control when testing a biological indicator (700) from a previously performed sterilization cycle. When a user selects an indicator (700) to scan, indicator analyzer (102, 800, 950) will verify (block 212) that a control indicator has been analyzed from the same lot or group as the selected indicator (700) by accessing data from server (106) via analyzer hub (104).

A control indicator (700) is a normal biological indicator (700) that has been selected from a group of associated biological indicators (700) and analyzed without first being run through a sterilization cycle and, if the group that the control has been selected from are viable indicators (700), will result in an indication of positive for contamination since it has not been sterilized. By testing a control from a group of indicators (700), a user may minimize the chance that a group of indicators (700) that have been stored or handled incorrectly will be unwittingly used with the system. By building controls to verify (block 212) that a control has been run for the selected indicator (700), the system can partially automate and enforce control testing. Once a control indicator (700) has been verified (block 212), the test indicator (700) may be analyzed (block 214) by indicator analyzer (102, 800, 950) by placing indicator (700) in a test well (810, 954) and allowing indicator analyzer (102, 800, 950) to incubate and analyze (block 214) the biological contents of indicator (700) to determine if contaminants survived a sterilization cycle. Once results are available from a test (block 214), the test may be finalized (block 216) by displaying results via touch screen display (850, 956) of the indicator analyzer (102, 800, 950), providing guidance or recommendations based upon the results; and transmitting results via the analyzer hub (104) to sterilizing cabinet (100), to server (106), or to both.

Figure 9:
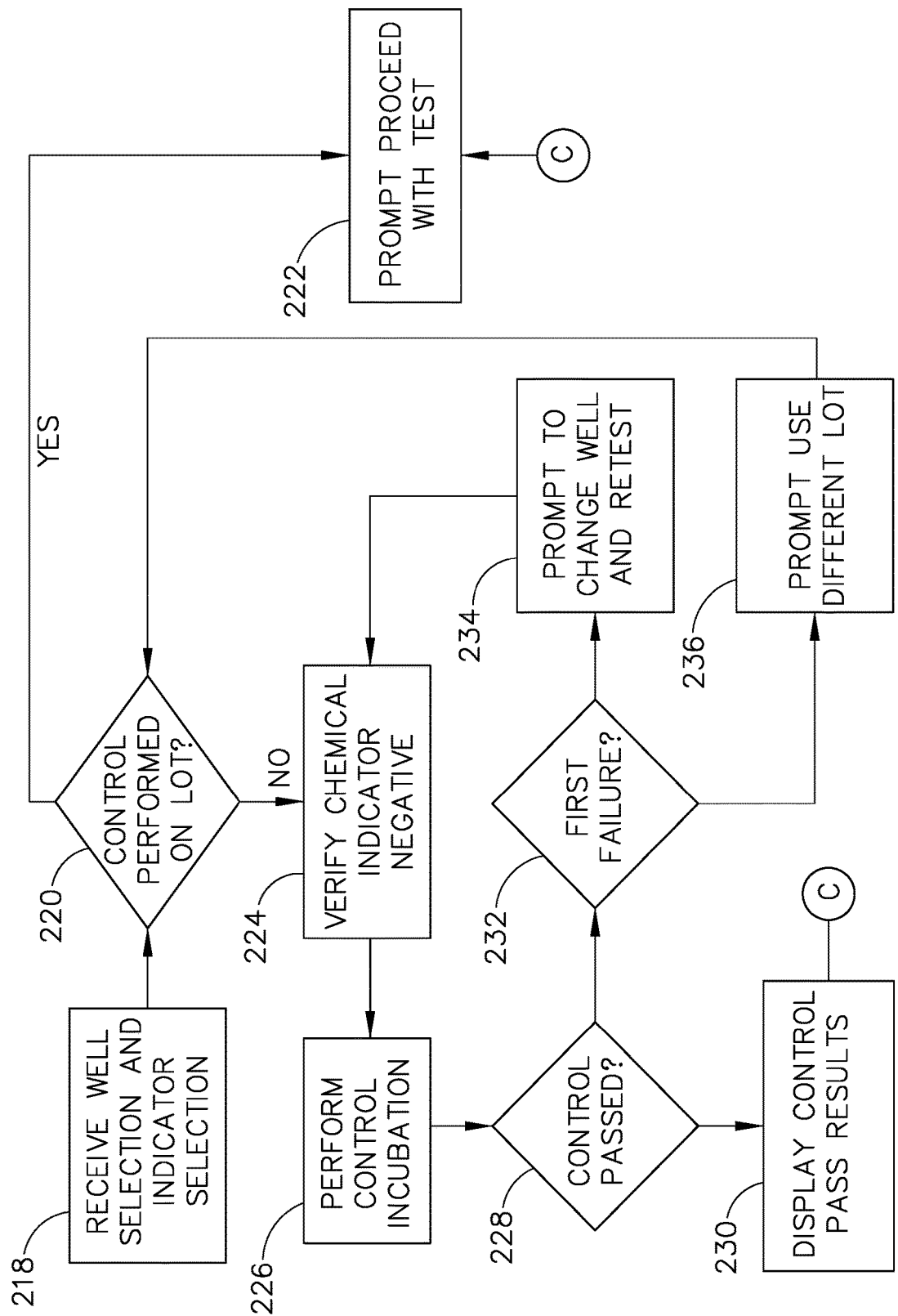
FIG. 9 depicts a flowchart of exemplary steps that may be performed by the indicator analyzer of FIG. 4 to enforce control indicator usage prior to normal testing.

FIG. 9 shows a set of exemplary steps that may be performed by indicator analyzer (102, 800, 950) to verify and enforce the use of a control indicator (700). A user may begin configuring an indicator test by making a selection via a user interface, such as touch screen display (850, 956) of indicator analyzer (102, 800, 950), resulting in a well (810, 954) selection and indicator (700) selection being received (block 218) by indicator analyzer (102, 800, 950). As noted above, indicator analyzer (102, 800, 950) may have multiple testing wells (810, 954) that can receive an indicator (700) and perform incubation and analysis such that multiple indicators (700) may be processed simultaneously. The indicator selection may be performed by scanning or reading a machine readable code or unique identifier on an indicator (700), using reader (870, 960); or by manual entry of indicator (700) information to allow indicator analyzer (102, 800, 950) to identify indicator (700). Identifying indicator (700) allows indicator analyzer (102, 800, 950) to access records on server (106) via analyzer hub (104) to determine whether the identified indicator (700) comes from a batch or group of indicators (700) that has been control tested; to determine if indicator (700) has already been incubated and analyzed and prevent erroneous retesting; or to identify a sterilization cycle that was performed with indicator (700).

Figure 12:
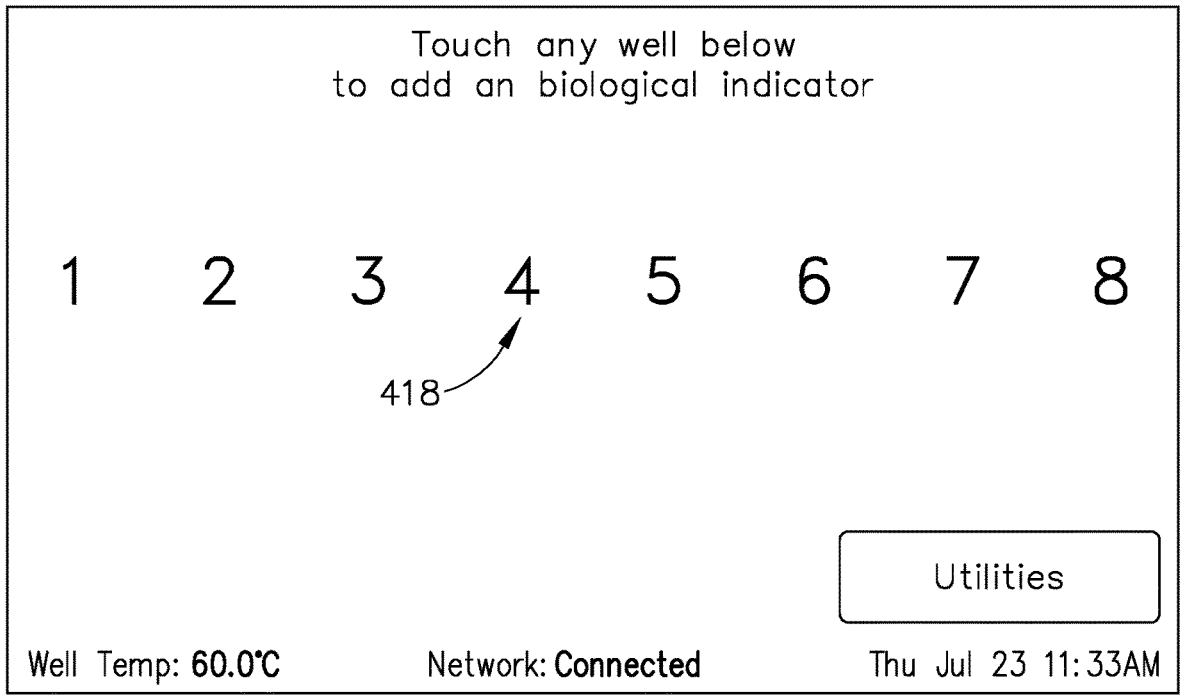
FIG. 12 depicts a screenshot of an exemplary user interface that could be presented via a display of the indicator analyzer of FIG. 4 to allow a user to select a well for analysis.

FIG. 12 shows a screenshot of an exemplary user interface for making a well (810, 954) selection. In the exemplary interface, eight different numbered wells (810, 954) are represented numerically and are selectable by interacting with the well number (418) (e.g., by tapping on the well number (418)) for the desired well (810, 954). Some implementations may include an exemplary user interface for selecting whether the selected well (810, 954) will receive a control indicator (700), by interacting with a "control" indicator button; or a test indicator (700), by interacting with a "test" indicator button. Some implementations may include an exemplary user interface for providing guidance to a user for scanning a machine identification from an indicator (700) via reader (870, 960) of indicator analyzer (102, 800, 950).

Figure 13:
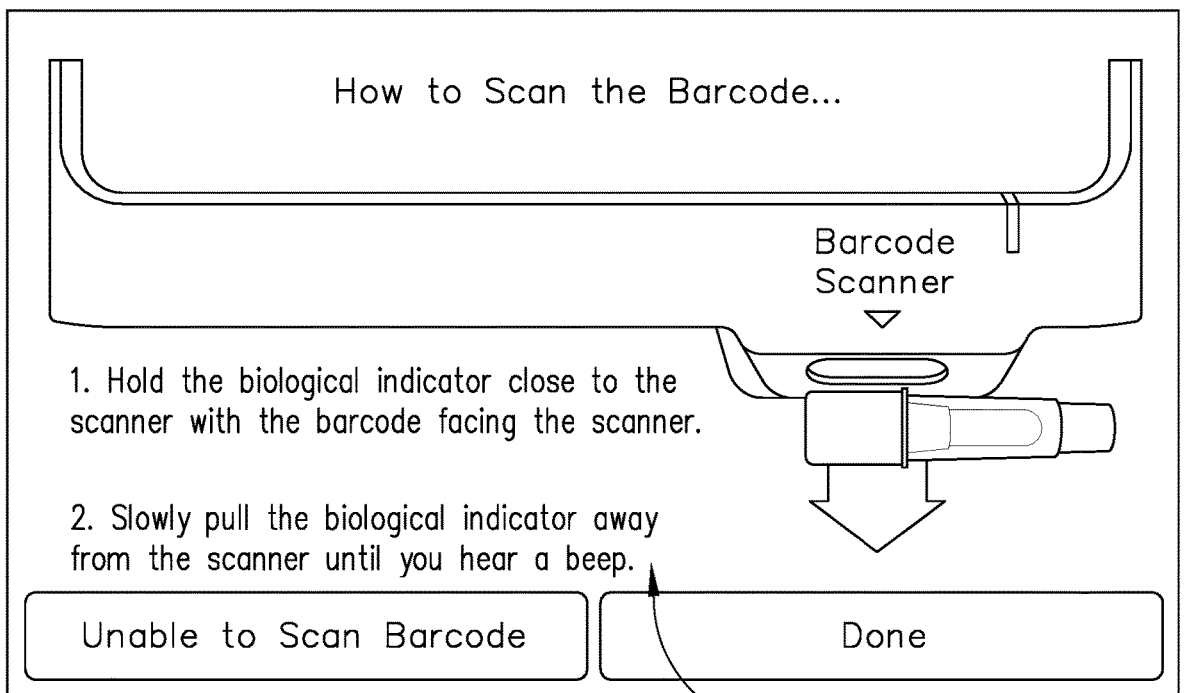
FIG. 13 depicts a screenshot of an exemplary user interface that could be presented via a display of the indicator analyzer of FIG. 4 to guide a user during barcode scanning of an indicator.

FIG. 13 shows a screenshot of an exemplary user interface for providing further guidance to a user (472) for scanning a machine identification from an indicator (700) via reader (870, 960) of indicator analyzer (102, 800, 950). This guidance may include activation of an arrow pointing to the location of reader (960) on indicator analyzer (950), with textual instructions on how to position indicator (700) in relation to reader (870, 960). In some versions, if an indicator analyzer (102, 800, 950) is being used in a setting where it cannot immediately communicate with server (106), or if reader (870, 960) is not available, identification information and sterilization cycle information may be entered manually via a user interface, which has manual entry boxes for inputting indicator (700) information and cycle information (e.g., identifying the particular sterilizing cabinet (100), the sterilization cycle type, the sterilization cycle number, the sterilization cycle start time, the sterilization cycle end time, etc.). This additional information will provide a link between a particular indicator (700) and a sterilization cycle that was previously carried out using sterilizing cabinet (100).

Once a well (810, 954) has been selected and an indicator (700) type has been selected (block 218), indicator analyzer (102, 800, 950) may query records from server (106) and identify a lot or group associated with the selected or scanned indicator (700) in order to determine if there has been a recent control indicator (700) analyzed from that lot or group (block 220). For example, if indicators (700) come in lots of 24, each of the 24 indicators (700) was likely manufactured at approximately the same time, from the same components, and was likely to be packaged, shipped, stored, and otherwise handled in a similar manner. Therefore, if a single indicator (700) from the lot of 24 is tested as a control indicator (700) and fails to report as positive for contamination, it may be likely that other indicators (700) from the same lot may be flawed as well, such that those indicators (700) should be discarded in order to avoid false negatives that would erroneously suggest that sterilization cycles were successful. The system may be configured so that indicator analyzer (102, 800, 950) requires a control indicator (700) to be analyzed for each lot, and the results recorded to server (106) and associated with the lot, so that the system can later verify the control (block 220). In some versions a control indicator (700) may be required once per lot, or once every 24 hours per lot, or any other variation on numbers per lot, durations of time between re-testing of control, or other similar configurable testing requirement.

If it is determined that control requirements have been met for the lot of the selected indicator (block 220), the control has been verified and the system may prompt the user to proceed with testing of selected test indicator (700). If it is determined that control requirements for the lot have not been met (block 220), the system will instead notify the user of the requirement for a control to be performed and guide the user through inserting a control indicator (700) from the selected lot into the selected well (810, 954). The system may additionally verify the chemical indicator (block 224) of the control indicator (700) via an interface screen that shows a graphic providing the difference in visual appearance between an unchanged chemical indicator and a changed chemical indicator. A chemical indicator of biological indicator (700) is initially a first color; but during a sterilization cycle a chemical reaction to temperatures or substances used during sterilization causes the chemical indicator to change to a second color, providing a visual indication as to whether a particular indicator (700) has undergone a sterilization cycle. Therefore, such an interface allows user to verify and indicate that a control indicator (700), which has not undergone a sterilization cycle, is still showing an original color through its chemical indicator. If a user selects otherwise, the system may prompt the user to select a different control indicator (700), as the previously selected control indicator (700) is either flawed or has been used in sterilization cycle.

Once the chemical indicator has been verified by the user and system (block 224), the system will begin to incubate the control indicator (block 226) after the control indicator (700) is inserted into the selected well (810, 954). Each well (810, 954) of indicator analyzer (102, 800, 950) may be equipped with a button, photo eye, or other sensor that allows it to determine when an indicator (700) is inserted into well (810, 954) so that incubation may automatically begin. In some versions, light source (830) and sensor (840) are used to determine when an indicator (700) is inserted into well (810, 954). Various suitable ways in which the presence of an indicator (700) in a well (810, 954) may be sensed will be apparent to those of ordinary skill in the art in view of the teachings herein.

Figure 14:
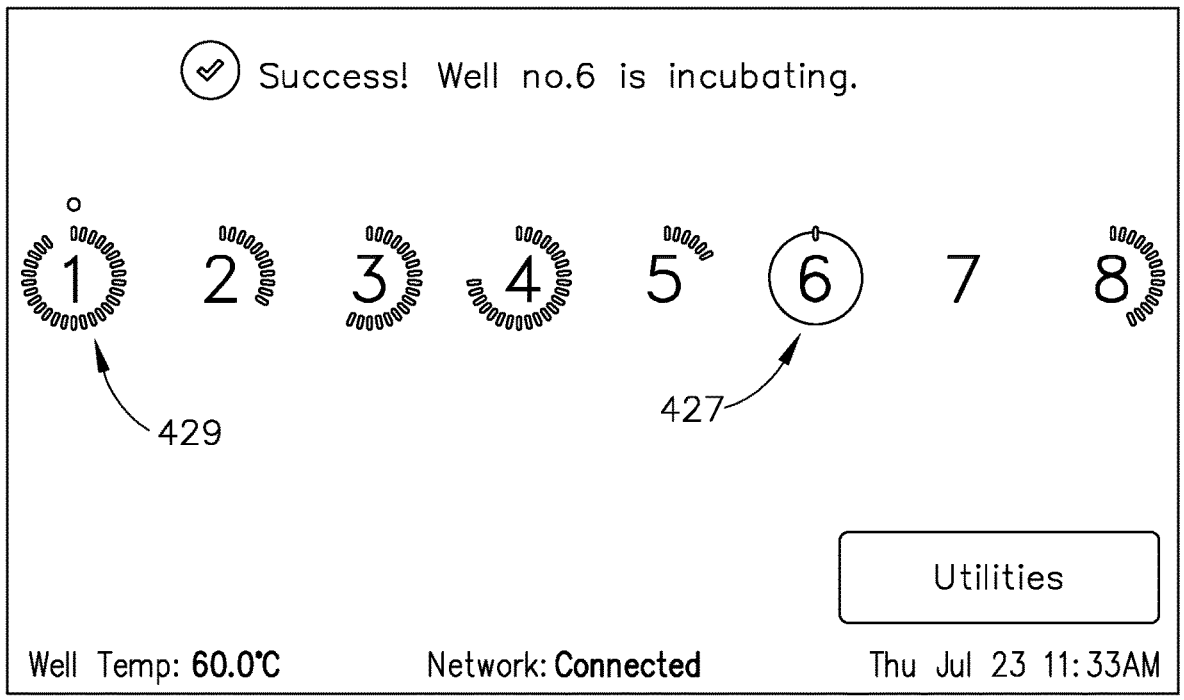
FIG. 14 depicts a screenshot of an exemplary user interface that could be presented via a display of the indicator analyzer of FIG. 4 to indicate to a user that one or more incubation and analysis are being performed.

FIG. 14 shows a user interface that could be displayed to provide updates to a user for each well (810, 954) of an indicator analyzer (102, 800, 950). In FIG. 14, eight wells (810, 954) are shown in varying states, with the incubation and analysis progress of each well (810, 954) shown by an incrementing series of dashes or other symbols (429); or with a colored circle or symbol (427) to indicate a recent change in status for a well (810, 954) that has recently started incubation or analysis, or has recently completed incubation or analysis. Selecting a particular well (810, 954) via the user interface of FIG. 14 may cause indicator analyzer (102, 800, 950) to display a more detailed status screen for the selected well (810, 954), which shows the type of test being performed so that a user may determine whether well (810, 954) is running a control indicator (700) or a test indicator (700), and a more detailed time status so that a user may get a more accurate picture of the remaining time for the incubation and analysis.

Once control indicator (700) incubation and analysis is complete (block 226), indicator analyzer (102, 800, 950) will determine if control indicator (700) tests positive for contamination, which indicates that the control indicator passed. If control indicator (700) results pass (block 228), the control indicator (700) results may be displayed (block 230) via touch screen display (850, 956) of indicator analyzer (102, 800, 950) and transmitted to server (106) to be associated with the lot from which the control indicator (700) was selected so that future test indicators (700) from that lot may be analyzed without interruption. If it is determined that the control failed (block 228), the system will notify a user of the failure, and this notification may indicate the well (810, 954) where the failed control indicator (700) is placed. If it is a first control failure (block 232), the system will indicate that it is a first failure and prompt the user to change wells (810, 954) and test a second control indicator (block 234).

An interface could be shown in the event of a first control indicator (700) failure. By way of example only, such an interface may provide additional guidance to a user to identify the lot that the second control should be selected from; as well as which well (180, 954) to avoid using in a second control. Performing a second control indicator (700) test in a different well (180, 954) allows the system to isolate for a malfunctioning test well (180, 954).

As another merely illustrative example, an interface may allow for identifying a user and guiding the user through performing a second control indicator analysis. The user identification may be used by system administrators to audit the results of the control indicator (700) analysis and ensure that proper steps are taken in the event of a control indicator (700) failure. Following the provided directions, the user may select a new control indicator (700) and return to the step of verifying the chemical indicator (block 224). If proceeding through the steps results in a second control failure (block 228), the system may instead prompt the user to discard the lot from which the previous failed controls were selected from and run a control and test indicator (700) from a different lot (block 236), which may require that the user rerun a sterilization cycle for affected medical devices with a new test indicator (700) from a different lot so that a valid control can be performed for the lot (block 220).

An interface could be displayed in the event of a second control indicator (700) failure. By way of example only, such an interface may provide the user with guidance for handling the second control indicator (700) failure. An additional user interface may be used to identify a user for audit purposes and provide additional guidance in the event of a second control indicator failure.

Figure 10:
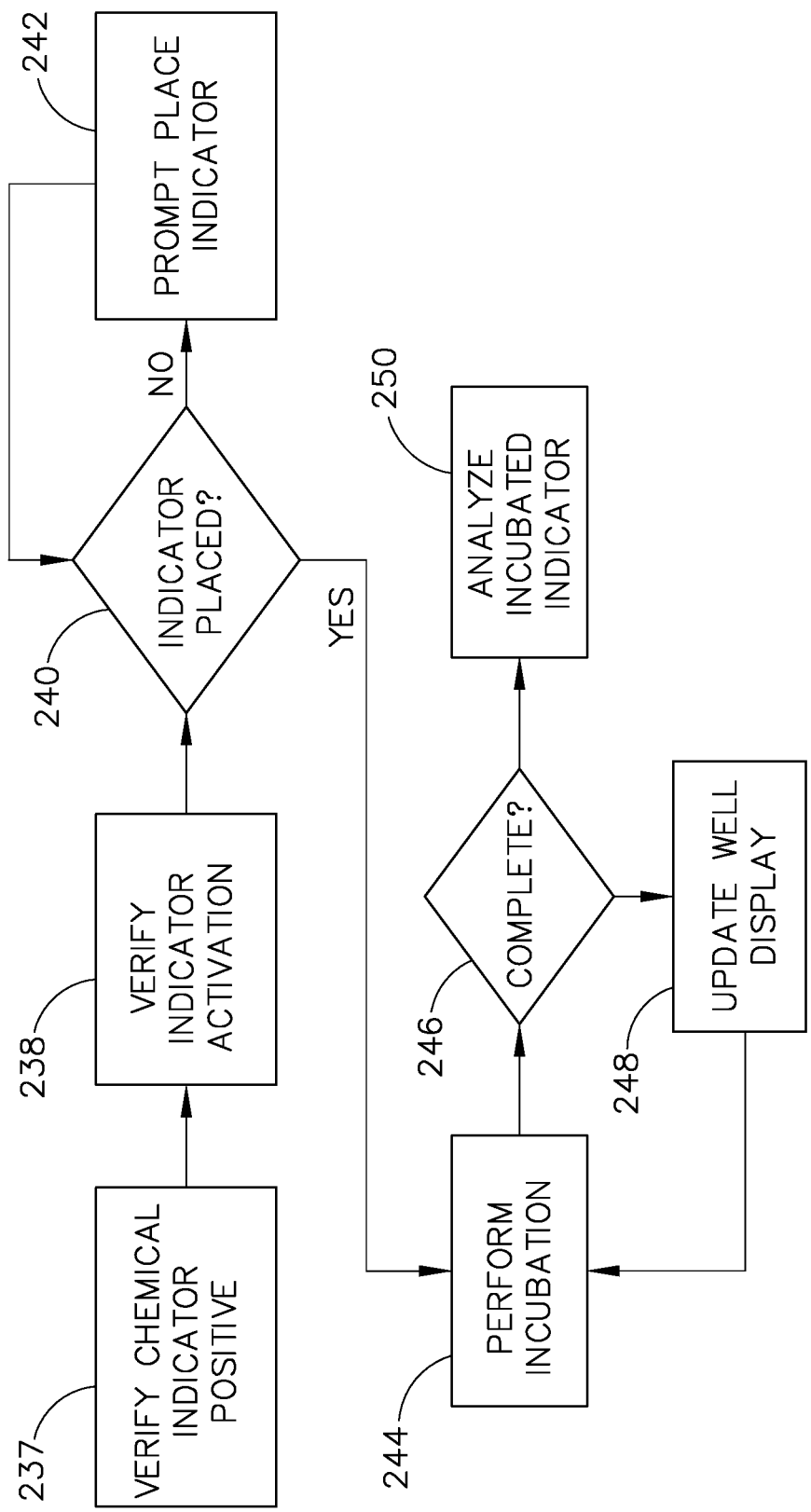
FIG. 10 depicts a flowchart of exemplary steps that may be performed by the indicator analyzer of FIG. 4 to incubate and analyze a test indicator.

FIG. 10 shows a set of exemplary steps that may be performed by indicator analyzer (102, 800, 950) to perform an incubation and test (block 214) on a test indicator (700) after a control indicator (700) has been verified (block 212). Initially, indicator analyzer (102, 800, 950) may verify that the chemical indicator of test indicator (700) shows positive for having undergone a sterilization cycle (block 237). In some instances, touch screen display (850, 956) may provide an interface screen that provides a user with guidance as to whether a chemical indicator is showing an original color or is showing a color indicative of a sterilization cycle; and to receive a selection from the user verifying that the chemical indicator shows positive (block 237) for having undergone a sterilization cycle. Such an interface screen may include graphical representations of indicator (700) with the different colors, with associated input buttons to indicate which color is being observed by the user.

Figure 15:
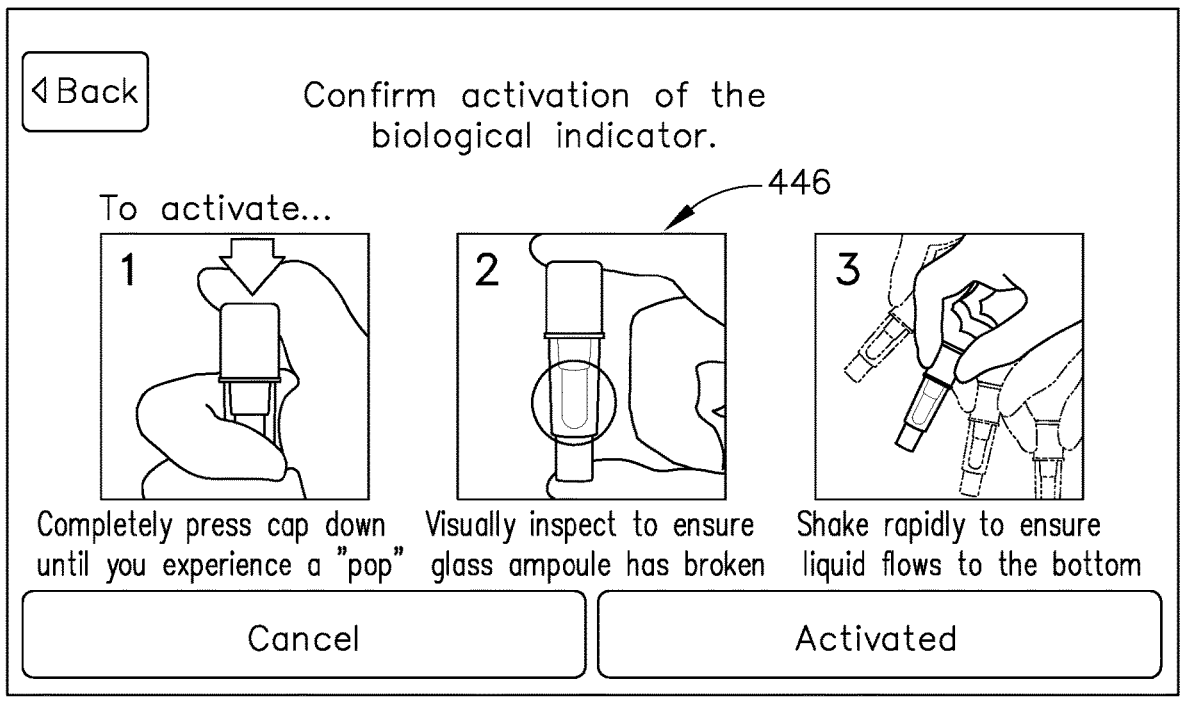
FIG. 15 depicts a screenshot of an exemplary user interface that could be presented via a display of the indicator analyzer of FIG. 4 to guide a user through activating an indicator.

Indicator analyzer (102, 800, 950) may also verify indicator (700) activation with the user (block 238) via a user interface such as that shown in FIG. 15, which provides an illustrated guide (446) for activating and verifying activation of a test indicator (700) prior to incubation and analysis, and for receiving a selection from the user verifying activation (block 238). After indicator activation has been verified (block 238), indicator (700) may be placed (block 240) into the selected test well (810, 954). An interface could be displayed to prompt (block 242) a user to place indicator (700) in the selected test well (810, 954) via a textual and/or graphic instruction, if a sensor of test well (810, 954) does not detect that indicator (700) has been placed (block 240). When a sensor of test well (810, 954), such as a button or photo eye, determines that indicator (700) has been placed (block 240), the incubation may be performed (block 244).

While waiting for the incubation to complete (block 246), indicator analyzer (102, 800, 950) will update well display screens (block 248) regularly so that users may review information on active wells (810, 954). Some exemplary interfaces could be maintained and updated (block 248) to reflect current information on well (810, 954) status. FIG. 16 shows an additional user interface that could be displayed via touch screen display (850, 956) of indicator analyzer (102, 800, 950) to provide more verbose information (450) on an indicator (700) currently being incubated and analyzed in a well (810, 954). Such verbose information could include, for example, the type of biological indicator (700) that is being analyzed, such as a control indicator (700) or test indicator (700), lot number from which indicator (700) was selected, serial number, expiration date, user identification, time that incubation began, date of incubation, verification of chemical indicator status, temperature of incubator, result of incubation and analysis if available, sterilization cycle associated with indicator (700), cycle type, cycle number, cycle start and end time, and other information that may desirably be displayed via indicator analyzer (102, 800, 950).

When incubation is complete (block 246) indicator analyzer (102, 800, 950) may analyze the incubated indicator (700) and determine if any biological contaminants developed or remain after the incubation (block 250). As noted above, in some versions, indicator (700) will contain a liquid solution that will react to biological contaminants such that if a first color is shown there is no contamination, indicating that the sterilization cycle was successful; and if a second color is shown there is contamination, indicating that the sterilization cycle failed. In such versions, analysis of whether indicator (700) is positive or negative for contamination may be performed by use of light source (830) and sensor (840), to detect fluorescence by indicator (700), as described above.

Figure 11:
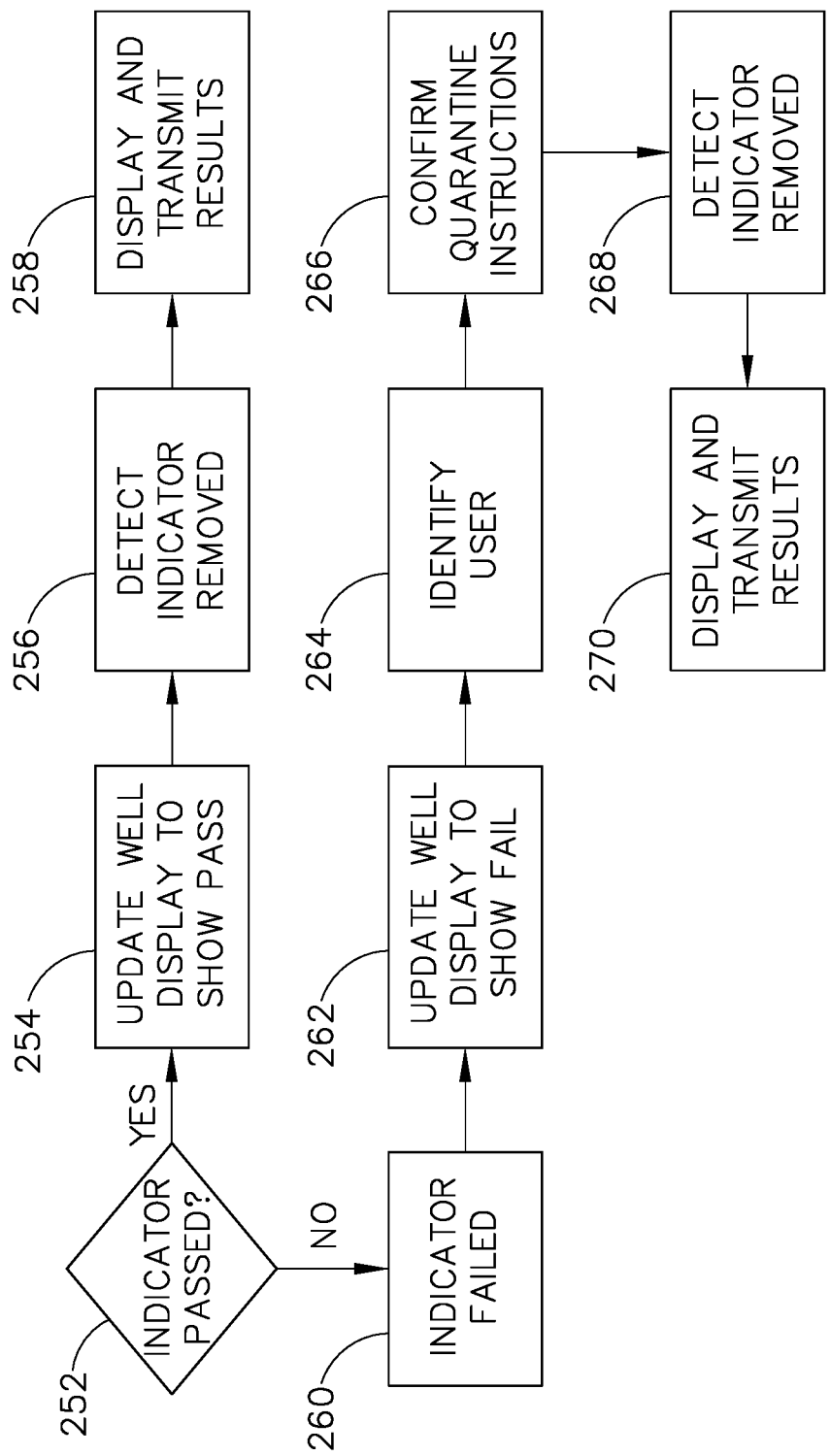
FIG. 11 depicts a flowchart of exemplary steps that may be performed by the indicator analyzer of FIG. 4 to finalize and display the results of an analysis.

FIG. 11 shows a set of exemplary steps that may be performed to display test results and finalize a test (block 216). If the indicator analysis (block 250) indicates that the test indicator (700) is negative for contamination, then indicator (700) has passed (block 252) and indicator analyzer (102, 800, 950) may update the well display interface to indicate to the user that a test indicator (700) has passed (block 254). An interface could be displayed indicate to a user that a well of the indicator analyzer (102, 800, 950) has completed a with a negative contamination result. The well indicator may be configured with a specific color signifying success, such as green; and/or may include a particular symbol signifying success, such as a checkmark, star, or other symbol, color, or visual indicator.

An interface may be displayed to give a user a more detailed description and guidance after a passed indicator (block 252). Indicator analyzer (102, 800, 950) may then detect when indicator (700) is removed from the test well (block 256) via a sensor situated in test well (810, 954); and display and transmit results (block 258) of the test indicator analysis. In some versions, the results are transmitted (block 258) from indicator analyzer (102, 800, 950) to communication hub (104) in response to a query from communication hub (104), such that the results are pulled from biological indicator analyzer (102, 800, 950) by communication hub (104). In some other versions, the results are pushed to communication hub (104) (block 258) by biological indicator analyzer (102, 800, 950), without requiring a query from communication hub (104).

An interface may provide a detailed summary of test results including information such as whether the completed test was for a control indicator (700) or a test indicator (700), a lot number from which indicator (700) was selected, serial number, expiration date, and other similar information as is shown and described in relation to the status interfaces described above. The same interface may provide information on the sterilization cycle, including but not limited to an identification of the sterilization cabinet (100) in which the sterilization cycle was performed, the type of sterilization cycle performed, the sterilization cycle number, the sterilization cycle start time, the sterilization cycle end time, etc. Results of the test indicator analysis may additionally be printed, stored locally on indicator analyzer (102, 800, 950), transmitted to a sterilizing cabinet (100) via analyzer hub (104), and/or transmitted to a remote sever (106) via analyzer hub (104).

If the indicator analysis (block 250) instead indicates that indicator (700) is positive for contamination, the system determines that indicator (700) failed (block 260) and may update the well display of indicator analyzer (102, 800, 950) to reflect the failure (block 262). An interface could be displayed to indicate to a user that an indicator (700) in a specific well failed, and to receive a confirmation or acknowledgment of the failure from the user.

An interface may be displayed to a user after an indicator (700) failure (block 260) in order to provide additional information and guidance for the user. Another interface may be displayed to a user in order to receive (block 264) an identification of the user for audit and follow up purposes, and to provide (block 266) additional guidance on quarantine and re-sterilization procedures for affected equipment. Identification of the user (block 264) may be useful where an administrator later wishes to ensure that quarantine procedures were correctly followed.

An interface could be displayed in order to receive a confirmation from a user that quarantine procedures or instructions were read and acknowledged. (block 266). Indicator analyzer (102, 800, 950) may then display a user interface in order to prompt a user to remove the failed indicator. Indicator analyzer (102, 800, 950) may detect the removal of the indicator (block 268) via a sensor of indicator analyzer (102, 800, 950) and display and transmit test results (block 270) in response. In some versions, the results are transmitted (block 270) from indicator analyzer (102, 800, 950) to communication hub (104) in response to a query from communication hub (104), such that the results are pulled from biological indicator analyzer (102, 800, 950) by communication hub (104). In some other versions, the results are pushed to communication hub (104) (block 270) by biological indicator analyzer (102, 800, 950), without requiring a query from communication hub (104).

An interface could be displayed to provide a verbose summary of test results that could include information such as test type, lot number, serial number, lot expiration date, sterilization cycle information, and additional information. Information generated from the failed test may also be printed, stored locally on the indicator analyzer (102, 800, 950), or transmitted to one or more of the server (106) and sterilizing cabinet (100) via the analyzer hub (104). Test results from a failed test may be used by sterilizing cabinet (100), the server (106), or both to identify medical devices that may need to be quarantined or re-sterilized, to identify sterilizing cabinets (100) that are malfunctioning, to identify users that are not following proper sterilization procedures, or to identify other associations with data stored on server (106) or sterilizing cabinet (100) that may be used to improved the effectiveness of future sterilization cycles.

C. Exemplary Enzyme Analysis Methods

Figure 17:
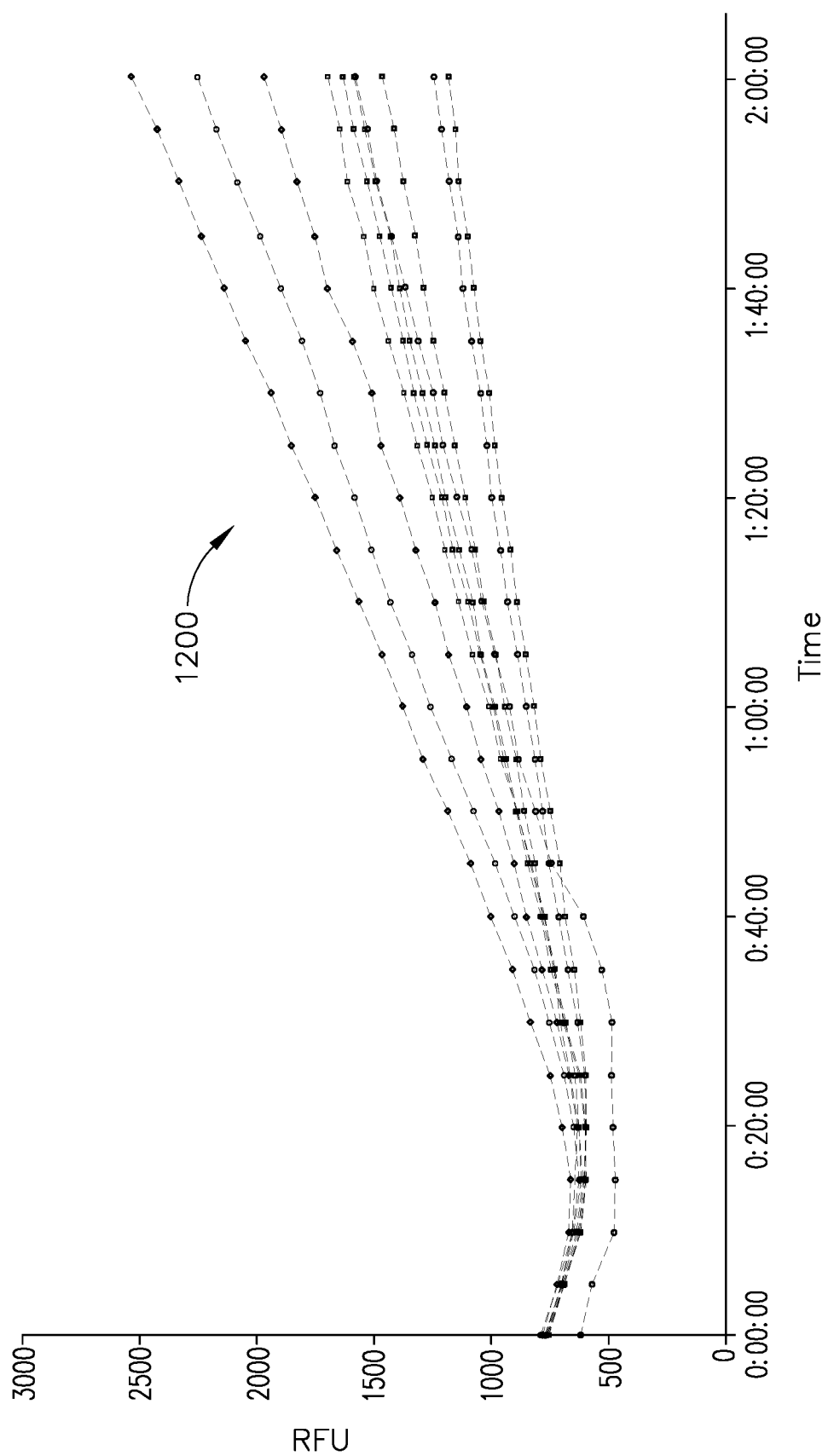
FIG. 17 depicts a graph showing a plot of relative fluorescence units over time for several biological indicators having active enzyme contained therein as detected by the indicator analyzer of FIG. 4.

As discussed above, indicator analyzer (102, 800, 950) is configured to analyze biological indicators (700) in order to determine whether active enzymes are present in fluid (732), by detecting fluorescence of fluid (732). This is accomplished by activating light source (830) and using sensor (840) to detect any fluorescence in fluid (732) in response to illumination from light source (830) during the incubation period in well (810, 954). FIG. 17 shows the fluorescence of a first group (1200) of biological indicators (700) over a period time (i.e., during an incubation period), as detected by indicator analyzer (102, 800, 950). The biological indicators (700) of first group (1200) were subject to a non-efficacious sterilization cycle in sterilization cabinet (100). In FIG. 17, the fluorescence is shown in relative fluorescence units (RFUs), which are known units of measurement. As can be seen, the fluorescence value drops during the initial part of the incubation period. By way of example only, this drop in fluorescence may be due to heating of fluid (732) in well (810, 954) of indicator analyzer (102, 800, 950). After this initial drop, the fluorescence value increases over the remainder of the incubation period. This increase in fluorescence value indicates that each biological indicator (700) of the first group (1200) contains an active enzyme. Thus, the sterilization processes encountered by biological indicators (700) of the first group (1200) were failures.

Figure 18:
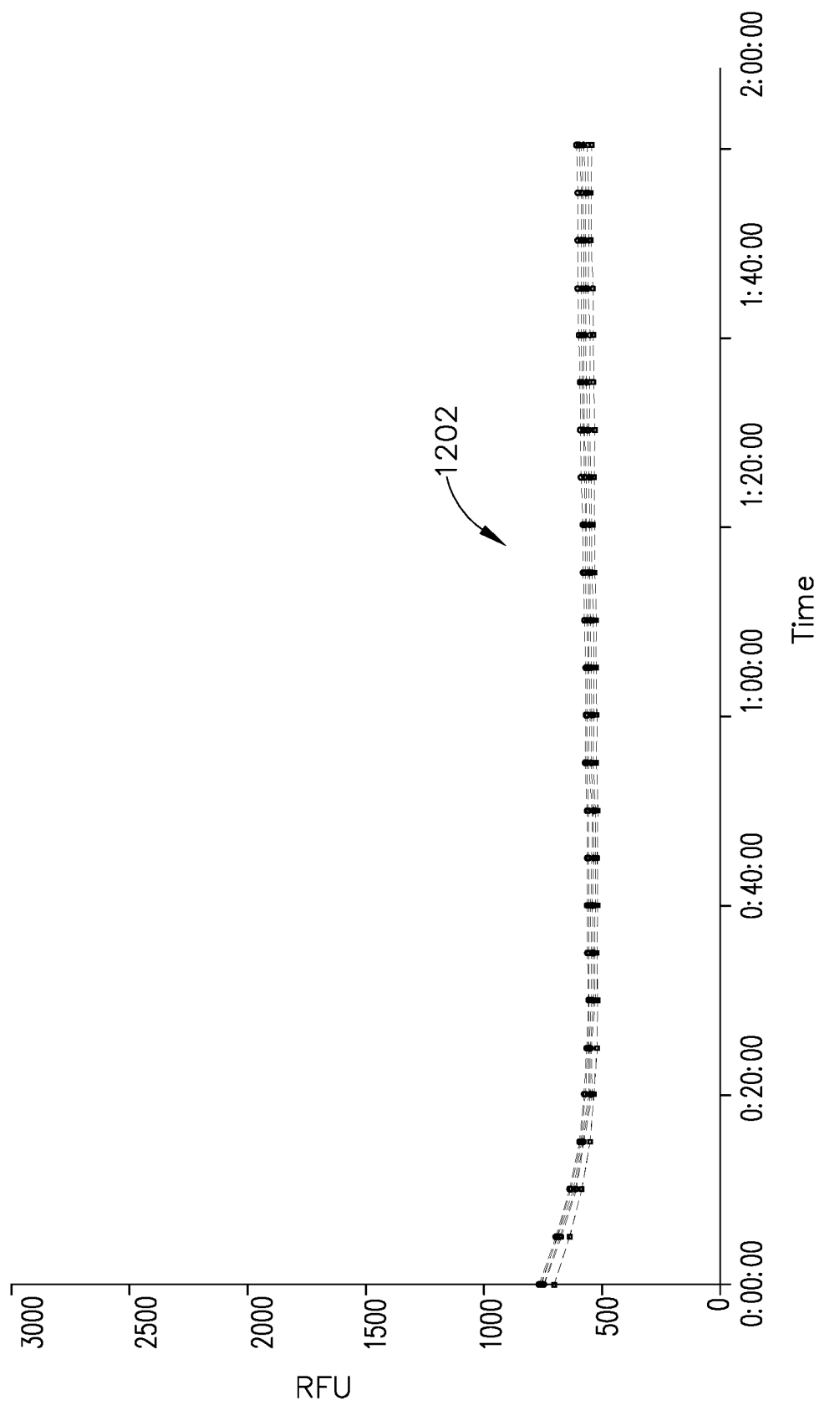
FIG. 18 depicts a graph showing a plot of relative fluorescence units over time for several biological indicators having inactive enzyme contained therein as detected by the indicator analyzer of FIG. 4.

FIG. 18 shows the fluorescence of a second group (1202) of biological indicators (700) over a period time (i.e., during an incubation period), as detected by indicator analyzer (102, 800, 950). The biological indicators (700) of second group (1202) were subject to an efficacious sterilization cycle in sterilization cabinet (100). In FIG. 18, the fluorescence is again shown in relative fluorescence units (RFUs). As can be seen, the fluorescence value drops during the initial part of the incubation period. As noted above, this drop in fluorescence may be due to heating of fluid (732) in well (810, 954) of indicator analyzer (102, 800, 950). After this initial drop, the fluorescence value stays substantially constant over the remainder of the incubation period. This constancy in fluorescence value indicates that none of the biological indicators (700) of the second group (1202) contains an active enzyme. Thus, the sterilization processes encountered by biological indicators (700) of the second group (1202) were successful.

In order to determine whether the fluorescence of biological indicators (700) will increase or remain substantially constant after the initial part of the incubation period where the fluorescence value drops, it may be desirable to monitor the fluorescence value for a substantial period of time in order for the results of the analysis to be sufficiently reliable or trustworthy. In other words, it may be desirable to continue monitoring the fluorescence value for a substantial period of time after the initial part of the incubation period where the fluorescence value drops, in order to determine with sufficient certainty that the fluorescence value has increased to a point indicating that active enzyme is present (indicating failure of the sterilization process); or that the fluorescence value has remained substantially constant indicating that no active enzyme is present (indicating success of the sterilization process). There may also be a competing interest in providing the analysis as quickly as possible in order to provide a satisfactory wait time for the end user. Thus, it may be desirable to provide analysis of biological indicators (700) as quickly as possible without compromising the reliability of the results of such analysis.

In order to speed up the analysis of biological indicators (700), it may be desirable to find the point at which the rate of product creation is at its maximum, then compare the maximum rate to a critical value. With an excess of substrate relative to enzyme concentration, this maximum rate may be directly related to the amount of enzyme present and thereby to the efficaciousness of the sterilization cycle.

Figure 19:
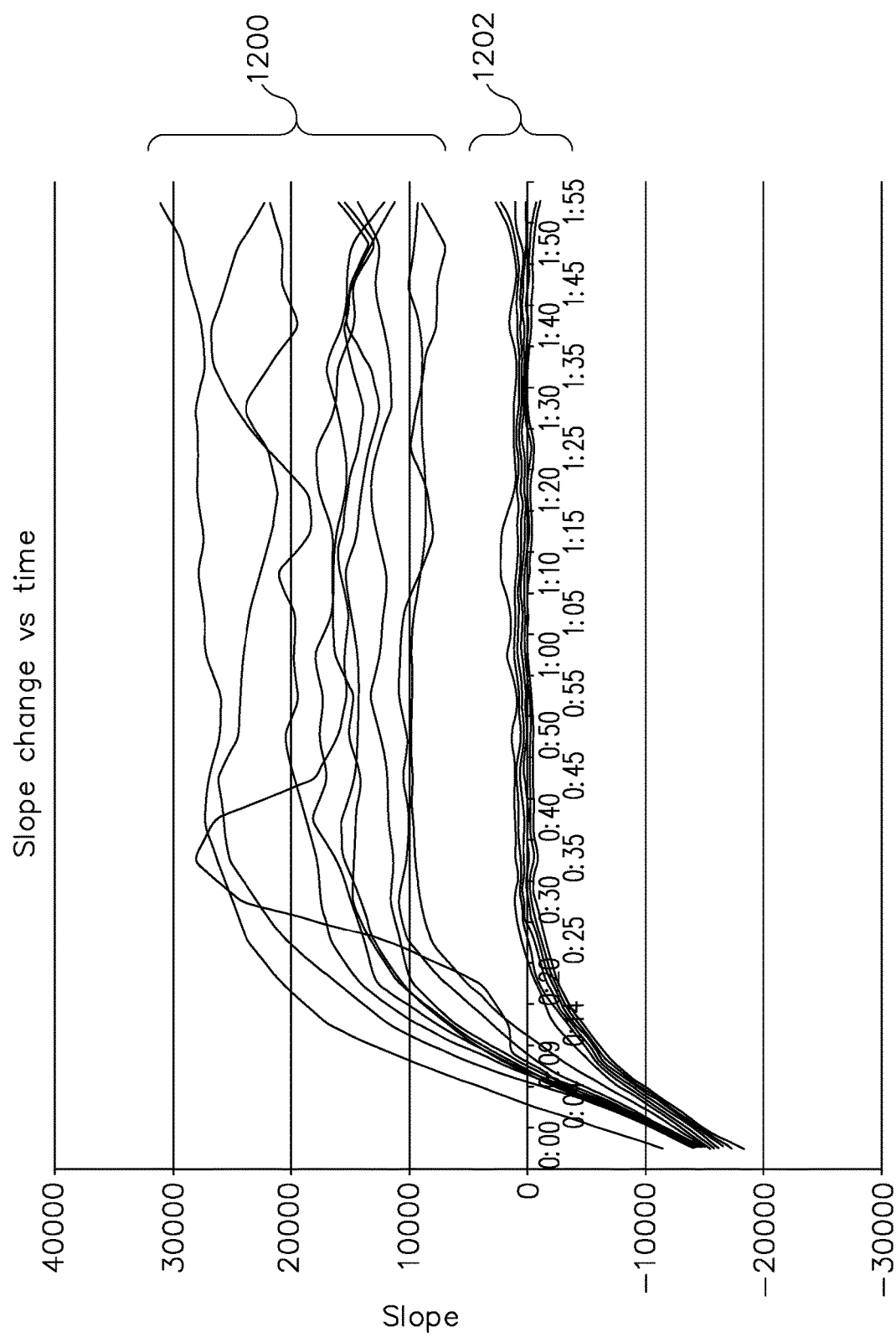
FIG. 19 depicts a graph showing a plot of the change in slope of the relative fluorescence units for the biological indicators of FIGS. 17 and 18.

As can be observed in FIGS. 17 and 18, the slopes of the curves are fairly constant after the initial drop. FIG. 19 shows the change in the slope over 15 minute increments of the data in FIGS. 17 and 18. As can be seen in FIG. 19, after about 20 minutes the slope reaches a maximum rate and then holds there for the two hour incubation period. While there is some noise in the reading, there is not a significant increase in the slope after 20 to 30 minutes. FIG. 19 also clearly illustrates the difference in the maximum slope for the first group (1200) versus the second group (1202). In particular, the average maximum slope for the first group (1200) is greater than 10,000; while the average maximum slope for the second group (1202) is approximately 1,600. This slope discrepancy is large enough that it may be easily detected in a reliable fashion. Moreover, this slope discrepancy may be detected rather quickly (e.g., on the order of approximately 20-30 minutes).

In view of the foregoing, rather than only tracking absolute fluorescence values, it may be beneficial to track the slopes associated with changes in fluorescence values. Tracking the slopes may provide relative rapid yet reliable analysis indicating whether a biological indicator (700) was subject to an efficacious sterilization cycle or a non-efficacious sterilization cycle. To this end, after an incubation period has begun in indicator analyzer (102, 800, 950), indicator analyzer (102, 800, 950) may initially monitor the fluorescence of biological indicator (700) and calculate the slope. Indicator analyzer (102, 800, 950) may then compare the slope against a critical value (e.g., some number that is greater than 1,600, such as 2,000; 5,000; 7,500; etc.). If the slope is greater than the critical value, then indicator analyzer (102, 800, 950) may conclude that an active enzyme is present in biological indicator (700); and trigger any of the various sterilization process failure notifications described herein. If the slope is less than the critical value, then indicator analyzer (102, 800, 950) may continue to monitor the slope until the slope reaches a maximum value. By way of example only, it may take approximately 20 to 30 minutes for the slope to reach a maximum value. If the slope is still less than the critical value at this stage, then indicator analyzer (102, 800, 950) may conclude that no active enzyme is present in biological indicator (700); and trigger any of the various sterilization process success notifications described herein.

While the foregoing examples have been provided in the context of monitoring fluorescence of fluid (732) in biological indicator (700), it should be understood that the same concepts may be readily applied to other detectable parameters (e.g., iridescence, absorbance, etc.) that change based on the presence of an active enzyme in fluid (732). Similarly, while the foregoing examples have been provided in the context of biological indicators (700) that have undergone sterilization processes in sterilization cabinet (100), it should be understood that the same concepts may be readily applied to any sterilization modality that uses an enzymatic reaction and/or in various other kinds of enzyme detection contexts.

Figure 20:
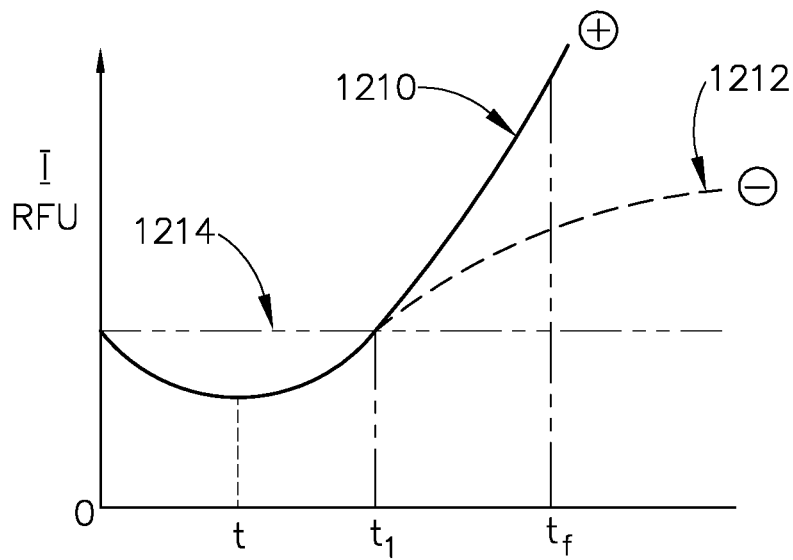
FIG. 20 depicts a graph showing a plot of relative fluorescence units over time, along with an associated formula that may be executed by the indicator analyzer of FIG. 4, associated with determining whether an active enzyme is present according to a first exemplary method.
Figure 21:
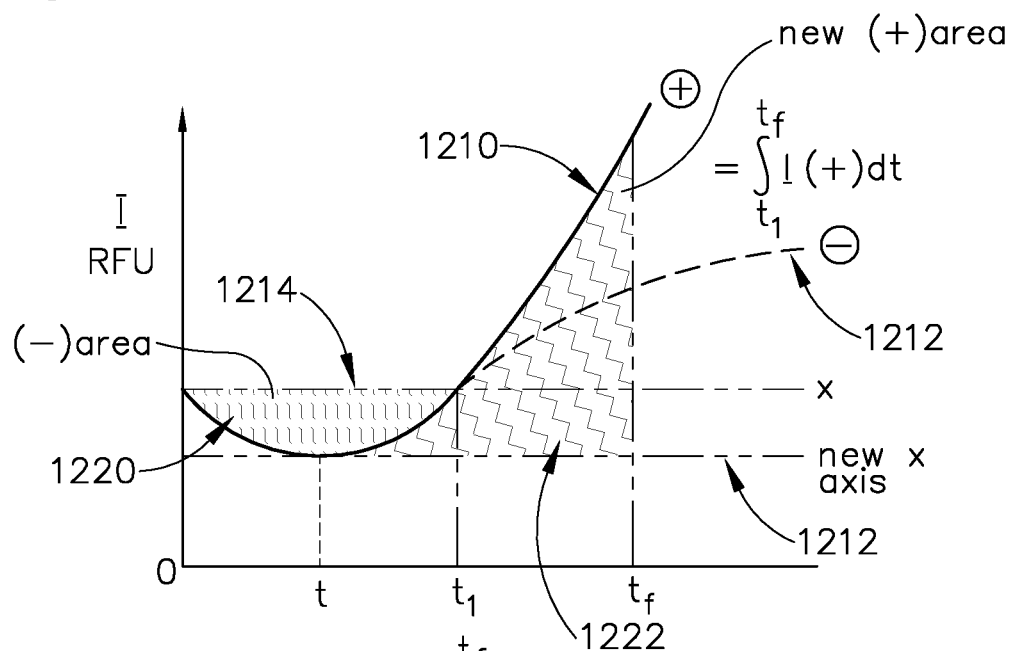
FIG. 21 depicts a graph showing a plot of relative fluorescence units over time, along with an associated formula that may be executed by the indicator analyzer of FIG. 4, associated with determining whether an active enzyme is present according to a second exemplary method.

FIGS. 20-21 show additional plots of fluorescence (in units of RFU) over time to illustrate additional exemplary methods of determining whether an active enzyme is present in fluid (732) of biological indicator (700). Just like the method described above with respect to FIGS. 17-19, the methods described below may be carried out using indicator analyzer (102, 800, 950). The methods associated with FIGS. 20-21 seek to filter out fluorescence data associated with the initial part of the incubation process where the fluorescence value encounters the initial drop (e.g., due to heating of fluid (732) in well (810, 954)). In both of the following examples, the variable t' is defined as the time at which the fluorescence value has completed the initial drop.

In the graph shown in FIG. 20, the curve (1210) is a plot associated with a biological indicator (700) having an active enzyme (indicating a non-efficacious sterilization cycle); while the curve (1212) is a plot associated with a biological indicator (700) lacking an active enzyme (indicating an efficacious sterilization cycle). The line (1214) is a horizontal line drawn parallel to the x-axis (which represents time), at the value associated with the initial fluorescence of biological indicator (700). The lower limit of the integral formula shown in FIG. 20, $t_1$, is taken at the point where line (1214) intersects curve (1210, 1212). The test statistic is given by the integral shown in FIG. 20.

In the graph shown in FIG. 21, the curve (1210) is again a plot associated with a biological indicator (700) having an active enzyme (indicating a non-efficacious sterilization cycle); while the curve (1212) is again a plot associated with a biological indicator (700) lacking an active enzyme (indicating an efficacious sterilization cycle). The line (1214) is again a horizontal line drawn parallel to the x-axis (which represents time), at the value associated with the initial fluorescence of biological indicator (700). Again, the lower limit of the integral formula shown in FIG. 21, $t_1$, is taken at the point where line (1214) intersects curve (1210, 1212). However, in this example t' is defined as the time at which the negative area (1220) (i.e., the area under line (1214) before reaching $t_1$) is halved; or alternatively at the centroid of the negative area (1220). This does not necessarily require finding the precise minimum value in curve (1210, 1212), but it still yields an integration starting point where the biologically relevant luminous intensity or fluorescence begins. The integration is then performed on the luminous intensity or fluorescence taken from $t_1$ to $t_f$, which represents the end of the incubation period analysis cycle, to generate the test statistic. As shown, this determines the area between curve (1210, 1212) and a new horizontal line (1216). This horizontal line is parallel to the x-axis and is at the value associated with the minimum fluorescence value associated with time t'.

Regardless of whether the test statistic is evaluated using the method described above with respect to FIG. 20 or the method described above with respect to FIG. 21, the test statistic may be compared to a predefined critical value. The critical value would serve as a threshold indicating whether biological indicator (700) contains an active enzyme or lacks an active enzyme. It should be understood that curve (1210) would yield a test statistic that exceeds the critical value, thereby indicating a non-efficacious sterilization cycle; while curve (1212) would yield a test statistic that falls below the critical value, thereby indicating an efficacious sterilization cycle. It should also be understood that the "trapezoidal method" may be used to perform integration in accordance with the methods described above. Various suitable ways in which a critical value may be identified for the purposes described herein will be apparent to those of ordinary skill in the art. It should also be understood that the fluorescence of biological indicators (700) may be analyzed using other techniques.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of processing a medical device, the method comprising: (a) receiving input from a user selecting a particular sterilization cycle from a plurality of available sterilization cycles; (b) identifying a particular kind of biological indicator associated with the selected sterilization cycle; (c) prompting the user to place the medical device and the identified biological indicator into a sterilization chamber of the sterilizing cabinet; (d) performing the selected sterilization cycle on the medical device in the sterilization chamber; and (e) determining whether the identified biological indicator contains any living organisms after performing the selected sterilization cycle.

Example 2

The method of Example 1, wherein the act of determining whether the identified biological indicator contains any living organisms comprises evaluating fluorescence associated with the identified biological indicator.

Example 3

The method of any one or more of Examples 1 through 2, wherein the act of determining whether the identified biological indicator contains any living organisms indicates that the identified biological indicator contains a living organism, the method further comprising informing the user that the identified biological indicator contains a living organism.

Example 4

The method of Example 3, wherein the act of informing the user that the identified biological indicator contains a living organism is performed via the sterilizing cabinet.

Example 5

The method of any one or more of Examples 1 through 4, wherein the act of determining whether the identified biological indicator contains any living organisms is performed using a biological indicator analyzer, wherein the biological indicator analyzer is separate from the sterilizing cabinet.

Example 6

A biological indicator analyzer, comprising: (a) a plurality of wells, wherein each well is configured to receive a respective biological indicator; (b) a plurality of organism detector features, wherein each organism detector feature is configured to detect whether a biological indicator disposed in a corresponding well of the plurality of wells contains a living organism; and (c) a touch screen, wherein the touch screen is configured to receive user input and provide information to the user indicating a status of biological indicator analysis.

Example 7

The biological indicator analyzer of Example 6, wherein the organism detector features comprise: (i) light sources configured to emit light toward biological indicators disposed in the wells, and (ii) sensors configured to detect fluorescence from biological indicators disposed in the wells.

Example 8

The biological indicator analyzer of any one or more of Examples 6 through 7, further comprising a communication port, wherein the communication port is configured to communicate results of biological indicator analysis to a device located remotely from the biological indicator analyzer.

Example 9

The biological indicator analyzer of any one or more of Examples 6 through 8, further comprising a plurality of indicator sensors, wherein each indicator sensor is configured to determine whether an indicator is placed in a corresponding well of the plurality of wells.

Example 10

The biological indicator analyzer of any one or more of Examples 6 through 9, further comprising: (a) a processor, wherein the processor is configured to receive a well selection and an indicator selection from a user and, in response, query a remote server to determine whether a control indicator has been tested for an indicator lot associated with the indicator selection and, where a control indicator has not been tested, display a control notification to the user via the touch screen; and (b) a memory in communication with the processor.

Example 11

The biological indicator analyzer of Example 10, wherein the processor is further configured to detect that a control indicator has been placed in a well, incubate the control indicator, and analyze the control indicator to determine if biological contamination is present, and, when biological contamination is present, display a notification via the touch screen indicating that the control indicator test was successful and associating the control indicator with the indicator selection.

Example 12

The biological indicator analyzer of Example 11, wherein the processor is further configured to, when biological contamination is not present in the control indicator, display a notification that a second control indicator must be run from the indicator lot in a different well.

Example 13

The biological indicator analyzer of any one or more of Examples 6 through 12, further comprising (a) a processor, wherein the processor is further configured to, in response to receiving a signal indicating that a user intends to place an indicator in a well, display a chemical indicator guide via the touch screen; wherein the chemical indicator guide is configured to display an original chemical indicator and a post-sterilization chemical indicator; wherein the processor is further configured to receive a selection from a user indicating whether the chemical indicator of the indicator matches the original chemical indicator or the post-sterilization chemical indicator; and (b) a memory in communication with the processor.

Example 14

The biological indicator analyzer of any one or more of Examples 6 through 13, further comprising (a) a processor, wherein the processor is further configured to, in response to receiving a signal indicating that a user intends to place an indicator in a well, display an indicator activation guide via the touch screen; wherein the indicator activation guide is configured to display a set of instructions for breaking a glass ampoule of the indicator, and mixing a chemical solution of the ampoule with the biological material; wherein the processor is further configured to receive a selection from a user indicating whether the glass ampoule is broken and whether the chemical solution has been mixed; and (b) a memory in communication with the processor.

Example 15

The biological indicator analyzer of any one or more of Examples 6 through 14, further comprising: (a) a processor, wherein the processor is configured to display a graphical representation of each well via the touch screen, wherein the graphical representation is configured to indicate whether an indicator is present in the corresponding well, the time remaining for a test being performed on an indicator in a corresponding well, and whether a test being performed in a corresponding well was a success or failure; and (b) a memory in communication with the processor.

Example 16

The biological indicator analyzer of any one or more of Examples 6 through 15, further comprising: (a) a processor, wherein the processor is configured to, in response to a failed indicator test, receive an identification from a user of the indicator analyzer, receive an acknowledgment of the failure from the user, display a set of quarantine instructions to the user via the touch screen, access a remote server in order to identify one or more surgical instruments associated with the failed indicator, and generate a notification comprising a description of the one or more surgical instruments associated with the failed indicator; and (b) a memory in communication with the processor.

Example 17

The biological indicator analyzer of any one or more of Examples 6 through 16, further comprising an indicator scanner, wherein the indicator scanner is operable to read an indicator identification from the biological indicator and determine an indicator data set based upon the indicator identification, wherein the indicator data set comprises a unique identifier and an indicator history.

Example 18

The biological indicator analyzer of Example 17, wherein indicator scanner is selected from the group consisting of an optical reader and a wireless radio reader.

Example 19

The biological indicator analyzer of any one or more of Examples 17 through 18, further comprising a processor and a communication port, wherein the processor is configured to provide an analysis result set to a server via the communication port, wherein the analysis result comprises a set of results data and the unique identifier.

Example 20

The biological indicator analyzer of any one or more of Examples 6 through 19, further comprising a housing defining the wells and containing the organism detector features, wherein the housing provides base configured to support the housing on a surface, wherein the touch screen is oriented obliquely relative to the base.

Example 21

A method for analyzing a biological indicator with an indicator analyzer, the method comprising: (a) presenting instructions to a user via a touch screen of the indicator analyzer; (b) receiving a biological indicator in a well selected from a plurality of wells in the indicator analyzer; (c) analyzing the biological indicator in the selected well, wherein the act of analyzing comprises evaluating fluorescence associated with the biological indicator in the selected well; (d) displaying results of the analysis via the touch screen; and (e) if the results of the analysis indicate that the biological indicator is not sterile, initiating a quarantine procedure.

Example 22

The method of Example 21, wherein verifying the control status of a biological indicator analysis comprises: (i) identifying a lot associated with the biological indicator, (ii) determining whether a control has been performed on the lot, and (iii) if the control has not been performed on the lot, then perform the following: (A) display an instruction for a user to place a control indicator in a well of the biological indicator analyzer, (B) perform a control analysis on the control, (C) if the control analysis fails the first time, then display an instruction for the user to repeat verifying the control status of the biological indicator using a different well, and (D) if the control analysis fails for the second time, then display an instruction for the user to repeat verifying the control status of the biological indicator using a different lot.

Example 23

The method of any one or more of Examples 21 through 22, wherein performing the biological indicator analysis comprises: (i) displaying an instruction for a user to verify that the biological indicator has undergone a sterilization cycle, (ii) displaying an instruction for a user to verify chemical activation of the biological indicator, (iii) determining whether the biological indicator has been placed in a well of the indicator analyzer, (iv) incubating the biological indicator, (v) emitting light towards the biological indicator from a light source of the indicator analyzer, and (vi) detecting fluorescence from the biological indicator using a sensor of the indicator analyzer.

Example 24

The method of any one or more of Examples 21 through 23, wherein the quarantine procedure comprises: (i) identifying a set of potentially contaminated medical devices, and (ii) for each potentially contaminated medical device of the set of the potentially contaminated medical devices, provide a notification to a responsible party for that potentially contaminated medical device.

Example 25

The method of claim 16, further comprising: (a) displaying an instruction for a user to scan the biological indicator using an indicator scanner of the indicator analyzer; (b)

receiving an indicator identification from the biological indicator; and (c) determining an indicator data set based upon the indicator identification, wherein the indicator data set comprises a unique identifier and an indicator history.

Example 26

A method for analyzing a biological indicator with an indicator analyzer, the method comprising: (a) verifying a control status of a biological indicator analysis by: (i) identifying a lot associated with the biological indicator, (ii) determining whether a control has been performed on the lot, and (iii) if the control has not been performed on the lot, the performing the following: (A) display an instruction for a user to place a control indicator in a well of the biological indicator analyzer, (B) perform a control analysis on the control, (C) if the control analysis fails the first time, then display an instruction for the user to repeat verifying the control status of the biological indicator using a different well, and (D) if the control analysis fails for the second time, then display an instruction for the user to repeat verifying the control status of the biological indicator using a different lot; (b) performing the biological indicator analysis by: (i) displaying an instruction for a user to verify that the biological indicator has undergone a sterilization cycle, (ii) displaying an instruction for a user to verify chemical activation of the biological indicator, (iii) determining whether the biological indicator has been placed in a well of the indicator analyzer, (iv) incubating the biological indicator, (v) emitting light toward the biological indicator from a light source of the indicator analyzer, and (vi) detecting fluorescence from the biological indicator using a sensor of the indicator analyzer; (c) distributing results of the biological indicator analysis; and (d) if the results of the biological indicator analysis indicate that the biological indicator is not sterile, then initiating a quarantine procedure.

VI. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for analyzing a biological indicator with an indicator analyzer, the method comprising:
   (a) receiving the biological indicator from an indicator lot in a well selected from a plurality of wells in the indicator analyzer, wherein the biological indicator comprises a carrier that provides a source of contamination;
   (b) determining, using a processor of the indicator analyzer, whether a control test has been performed for the indicator lot;
   (c) based on determining that the control test has not been performed for the indicator lot:
      (i) displaying a notification via a touchscreen display that indicates the control test should be performed, and
      (ii) performing the control test in one of the plurality of wells on an unsterilized control indicator from the indicator lot;
   (d) using an organism detector device of the indicator analyzer, analyzing the biological indicator in the well to detect contamination and produce a set of analysis data; and
   (e) displaying results of the analysis via the display based on the set of analysis data;
   wherein:
   (A) determining whether the control test has been performed for the indicator lot comprises receiving an indicator data set describing the biological indicator,
   (B) determining whether the control test has been performed for the indicator lot is based on the indicator data set, and
   (C) based on determining that the control test has not been performed for the indicator lot, preventing analyzing the biological indicator prior to the control test on the control indicator from the indicator lot.

2. The method of claim 1, further comprising, before analyzing the biological indicator:
   (a) displaying an instruction via the display for a user to verify that the biological indicator has undergone a sterilization cycle; and
   (b) displaying an instruction for a user to verify chemical activation of the biological indicator.

3. The method of claim 1, wherein analyzing the biological indicator in the well comprises:
   (i) incubating the biological indicator with an incubator of the well,
   (ii) emitting light towards the biological indicator from the organism detector device, and
   (ii) detecting fluorescence from the biological indicator using a sensor of the organism detector device.

4. The method of claim 1, further comprising performing a quarantine procedure in response to the set of analysis data indicating the presence of contamination in the biological indicator by:
   (i) identifying a sterilizing cabinet that performed a sterilization procedure with the biological indicator,
   (ii) identifying one or more surgical instruments associated with the sterilization procedure or the sterilizing cabinet, and
   (iii) providing a notification describing the one or more surgical instruments and the sterilizing cabinet.

5. The method of claim 1, further comprising:
   (a) displaying an instruction for a user to scan the biological indicator using an indicator scanner of the indicator analyzer prior to receiving the biological indicator in the well;

(b) receiving an indicator identification from the biological indicator via the indicator scanner; and
(c) determining an indicator data set based upon the indicator identification, wherein the indicator data set comprises a unique identifier and an indicator history;
wherein determining, using the processor of the indicator analyzer, whether the control test has been performed for the indicator lot is based on the indicator data set.

6. The method of claim 1, further comprising, after performing the control test on the unsterilized control indicator and before analyzing the biological indicator in the well to detect contamination and produce the set of analysis data:
(i) confirming the presence of biological contamination based on performing the control test on the unsterilized control indicator, and
(ii) upon a determination that biological contamination is present in the control indicator, displaying a notification via the display indicating that the control test was successful.

7. The method of claim 1, further comprising, upon a determination that biological contamination is present in the control indicator, updating an indicator data set that is associated with the control indicator to indicate that the control test was successful.

8. The method of claim 1:
(a) determining for the plurality of wells whether each of the plurality of wells is vacant or contains a received biological indicator using a plurality of indicator presence sensors; and
(b) displaying a well status via the display that indicates a vacancy status for each of the plurality of wells.

9. The method of claim 1, further comprising:
(a) displaying a chemical indicator guide via the display, wherein the chemical indicator guide comprises descriptions of an original chemical indicator and a post-sterilization chemical indicator; and
(b) receiving a selection indicating whether a chemical indicator of the biological indicator matches the original chemical indicator or the post-sterilization chemical indicator.

10. The method of claim 1, further comprising:
(a) displaying an indicator activation guide via the display, wherein the indicator activation guide comprises instructions for breaking a glass ampoule of the biological indicator and mixing a chemical solution of the ampoule with the source of contamination; and
(b) receiving a selection indicating whether the glass ampoule is broken and whether the chemical solution has been mixed.

11. The method of claim 1, further comprising:
(a) displaying a graphical representation of each well of the plurality of wells via the display;
(b) displaying, for each graphical representation, whether a corresponding well is vacant; and
(c) displaying, when the corresponding well is not vacant, a time remaining to finish analyzing a corresponding biological indicator in that corresponding well.

12. A method for analyzing a biological indicator with an indicator analyzer, the method comprising:
(a) receiving the biological indicator from an indicator lot in a well selected from a plurality of wells in the indicator analyzer, wherein the biological indicator comprises a carrier that provides a source of contamination;
(b) determining, using a processor of the indicator analyzer, whether a control test has been performed for the indicator lot;
(c) based on determining that the control test has not been performed for the indicator lot:
(i) displaying a notification via a touchscreen display that indicates the control test should be performed, and
(ii) performing the control test in one of the plurality of wells on an unsterilized control indicator from the indicator lot;
(d) using an organism detector device of the indicator analyzer, analyzing the biological indicator in the well to detect contamination and produce a set of analysis data; and
(e) displaying results of the analysis via the display based on the set of analysis data;
wherein the method further comprises, after performing the control test on the unsterilized control indicator and before analyzing the biological indicator in the well to detect contamination and produce the set of analysis data:
(A) confirming the presence of biological contamination based on performing the control test on the unsterilized control indicator, and
(B) upon a determination that biological contamination is present in the control indicator, displaying a notification via the display indicating that the control test was successful.

13. The method of claim 12, further comprising, before analyzing the biological indicator:
(a) displaying an instruction via the display for a user to verify that the biological indicator has undergone a sterilization cycle; and
(b) displaying an instruction for a user to verify chemical activation of the biological indicator.

14. The method of claim 12, wherein analyzing the biological indicator in the well comprises:
(i) incubating the biological indicator with an incubator of the well,
(ii) emitting light towards the biological indicator from the organism detector device, and
(ii) detecting fluorescence from the biological indicator using a sensor of the organism detector device.

15. The method of claim 12, further comprising performing a quarantine procedure in response to the set of analysis data indicating the presence of contamination in the biological indicator by:
(i) identifying a sterilizing cabinet that performed a sterilization procedure with the biological indicator,
(ii) identifying one or more surgical instruments associated with the sterilization procedure or the sterilizing cabinet, and
(iii) providing a notification describing the one or more surgical instruments and the sterilizing cabinet.

16. The method of claim 12, further comprising:
(a) displaying an instruction for a user to scan the biological indicator using an indicator scanner of the indicator analyzer prior to receiving the biological indicator in the well;
(b) receiving an indicator identification from the biological indicator via the indicator scanner; and
(c) determining an indicator data set based upon the indicator identification, wherein the indicator data set comprises a unique identifier and an indicator history;

wherein determining, using the processor of the indicator analyzer, whether the control test has been performed for the indicator lot is based on the indicator data set.

17. The method of claim 12, further comprising, upon a determination that biological contamination is present in the control indicator, updating an indicator data set that is associated with the control indicator to indicate that the control test was successful.

18. The method of claim 12, further comprising:
(a) determining for the plurality of wells whether each of the plurality of wells is vacant or contains a received biological indicator using a plurality of indicator presence sensors; and
(b) displaying a well status via the display that indicates a vacancy status for each of the plurality of wells.

19. The method of claim 12, further comprising:
(a) displaying a chemical indicator guide via the display, wherein the chemical indicator guide comprises descriptions of an original chemical indicator and a post-sterilization chemical indicator; and
(b) receiving a selection indicating whether a chemical indicator of the biological indicator matches the original chemical indicator or the post-sterilization chemical indicator.

20. The method of claim 12, further comprising:
(a) displaying an indicator activation guide via the display, wherein the indicator activation guide comprises instructions for breaking a glass ampoule of the biological indicator and mixing a chemical solution of the ampoule with the source of contamination; and
(b) receiving a selection indicating whether the glass ampoule is broken and whether the chemical solution has been mixed.

21. The method of claim 12, further comprising:
(a) displaying a graphical representation of each well of the plurality of wells via the display;
(b) displaying, for each graphical representation, whether a corresponding well is vacant; and
(c) displaying, when the corresponding well is not vacant, a time remaining to finish analyzing a corresponding biological indicator in that corresponding well.

* * * * *